(12) United States Patent
Willner et al.

(10) Patent No.: US 8,597,956 B2
(45) Date of Patent: Dec. 3, 2013

(54) METHOD AND DEVICE FOR DETECTION OF NITROAMINES

(75) Inventors: Itamar Willner, Mevasseret Zion (IL); Ran Tel-Vered, Jerusalem (IL); Michael Riskin, Jerusalem (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 13/512,380

(22) PCT Filed: Dec. 7, 2010

(86) PCT No.: PCT/IL2010/001033
§ 371 (c)(1),
(2), (4) Date: May 29, 2012

(87) PCT Pub. No.: WO2011/070572
PCT Pub. Date: Jun. 16, 2011

(65) Prior Publication Data
US 2012/0264222 A1    Oct. 18, 2012

(30) Foreign Application Priority Data
Dec. 7, 2009 (IL) .......................... 202569

(51) Int. Cl.
G01N 33/22 (2006.01)
G01N 33/00 (2006.01)
G01N 27/22 (2006.01)
G01N 21/55 (2006.01)

(52) U.S. Cl.
USPC ............... 436/98; 436/96; 436/91; 422/68.1; 422/82.01

(58) Field of Classification Search
USPC ................................. 436/98, 96, 91
See application file for complete search history.

(56) References Cited

U.S. PATENT DOCUMENTS

2011/0015872 A1    1/2011 Haick et al.

FOREIGN PATENT DOCUMENTS

WO    2009118739 A1    10/2009

OTHER PUBLICATIONS

Anarwal, G.S, Sutta Gupta, S. Phys, Rev. B 1985, 32, 3607.
Andrew, T.L.; Swager, T.M. J. Am. Chem. Sac. 2007, 129, 7254.
Bakaltcheva, I.B.; Ligler, F.S.; Patterson, C.H.; Shriver-Lake, L.C. Anal. Chim. Acta 1999, 399, 13.
Bart, J.C.; Judd, L.L.; Kusterbeck, A.W. Sens. Actuators. B 1997, 39, 411.
Berger, C.E.H.; Beumer, T.A.M.; Kooyman, R.P.H.; Greve, J. Anal. Chem. 1998, 70. 703.
Bossi, A.; Bonini, F.; Turner, A.P.F.; Piletsky, S.A. Biosens. & Bicelectron. 2007, 22, 1131.
Bromage, E.S.; Lackie, T.; Linger, M.A.; Ye, J.; Kaattari, S.L. Biosens. & Bioelectron. 2007. 22. 2532.
Cao, L.; Li, S. F. Y.; Zhou, X. C. Analyst 2001, 126, 184.
Cerruti, M.; Jaworski, J.; Raorane, D.; Zueger, C.; Varadarajan, J.; Carraro. C.; Lee, S.W.; Mabuodian, R.; Majumdar. A. Anal. Chem. 2009, 81, 4192.
Chang, C.-P.; Chao, C.-Y.; Huang, J.-H.; Li, A.-K.; Hsu, C.-S.; Lin, M.-S.; Hsieh, B.-R.; Su, A.-C. Synth. Met. 2004, 144, 297.
Chen, J.; Law, C. C. W.; Lam, J. W. Y.; Dong, Y.; Lo, S. M. F.; Williams, I. D.; Zhu, D.; Tang. B. Z. Chem. Mater. 2003, 15, 1535.

(Continued)

*Primary Examiner* — Christine T Mui
(74) *Attorney, Agent, or Firm* — Fleit Gibbons Gutman Bongini & Bianco PL; Martin Fleit; Paul D. Bianco

(57) ABSTRACT

An ultrasensitive method for detecting non-aromatic non-planar nitroamine analytes in a sample is provided.

16 Claims, 11 Drawing Sheets

(56) References Cited

OTHER PUBLICATIONS

Choi, Y,; Ho, N.-H.; Tung, C.-H. Angew. Chem., Int. Ed. 2007, 46, 707.
Content, S.; Trogler, W. C.; Sailor, M. J. Chem.sEur. J. 2000, 6, 2205.
Daniel, M.-C.; Astruc, D. Chem. ReV. 2004, 104, 293.
Doron, A.; Katz, E.; Willner, I. Langmuir 1995, 11, 1313.
Fireman-Shoresh, S.; Turyan, I.; Mandler, D.; Avnir, D.; Marx. S. Langmuir 2005, 21, 7842.
Freeman, R.; Willner, I. Nano Lett. 2009, 89, 322.
Gao, D.;Wand, Z.; Liu, B.; Ni, L.; Wu, M.; Zhang, Z. Anal. Chem. 2008, 80, 8545.
Gordon, R.; Sinton, D.; Kavanagh. K.L.; Brolo, A.G. acc. Chem. Res. 2008, 41, 1049.
Haupt, K. Analyst, 2001, 126, 747.
Haupt, K.; Mosbach, K. Chem. ReV. 2000, 100, 2495.
He, L.; Musick, M.D.; Nicewarner, S.R.; Sallinas, F.G., Benkovic, S.J.; Natan, M J.; Keating, C.D. J. Am. Chem . Soc. 2000, 122, 9071.
Homola, J. Cehm. Rev. 2008, 108, 462.
Hrapovic, S.; Majid, E.; Liu, Y.; Male, K.; Luong, J. H. T. Anal. Chem. 2006, 78, 5504.
Hu, W. P.; Chen, S.-J.; Huang, K.-T.; Hsu, J. H.; Chen, W. Y.; Chang, G. L.; Lai, K.-A. Biosens. Bioelectron. 2004, 19, 1465.
Hu, X.; An, Q.; Li, G.; Tao, S.; Liu, J. Angew. Chem., Int. Ed. 2006, 45, 8145.
Jiang, G.; Baba, A.; Ikarashi, H.; Xu. R.; Locklin, J.; Kashif, K. R.; Shinbo, K.; Kato, K.; Kaneko, F.; Advincula, R. J. Phys. Chem. C 2007, 111, 18687.
Jiang, Y.; Zhao, H.; Zhu, N.; Lin, Y.; Yu, P.; Mao. L. Angew. Chem. Int. Ed. 2009, 47, 8601.
Kannan, G.K.; Nimal, A.T.; Mittal, U.;Yadava, R.D.S.; Kapoor, J.C. Sens. Actuators, B 2004, 101, 328.
Kirsch, N.; Hart, J. P.; Bird, D. J.; Luxton, R. W.; McCalley, D. V. Analyst 2001, 126, 1936.
Knoll, W. Annu. Rev. Phys. Chem. 1998, 49, 569.
Krause, A.R.; Van Neste, C.; Senesac, T.; Thundat, E.; Finot, E. J. Appl. Phys. 2008, 103, 094906.
Lahav, M.; Gabai, R.; Shipway, A. N.; Willner, I. Chem. Commun. 1999, 19, 1937.
Lahav, M.; Kharitonov, A. B.; Katz, O.; Kunitake, T.; Willner. I. Anal. Chem. 2001. 73, 720.
Lahav, M.; Shipway, A. N.; Willner, I.; Nielsen, M. B.; Stoddart, J. F. J. Electroanal. Chem. 2000, 482, 217.
Larsson, A.; Angbrant, J.; Ekeroth, J.; Mansson, P.; Liedberg, B. Sens. Actuators, B 2006, 113, 730.
Li, X.; Husson, S. M. Biosens. Bioelectron. 2006, 22, 336.
Raitman, O. A.; Chegel, V. I.; Kharitonov, A. B.; Zayats, M.; Katz, E.; Willner, I. Anal. Chim. Acta 2004, 504. 101.
Liang, H.-J.; Ling, T.-R.; Rick, J. F.; Chou, T.-C. Anal. Chim. Acta 2005, 542, 83.
Lyon, L.A.; Musick, M.D.; Natan M. J. Anal. Chem. 1998, 70, 5177.
Lyon, L.A.; Musick, M.D.; Smith, P.C.; Reiss, B.D.; Pena, D.J.; Natan, M.J. Sens. Actuators, B 1999, 54, 118.
Matsui, J.; Akarnatsu, K.; Hara, N.; Miyoshi, D.; Nawafune, H., Tamaki, K., Sugimoto, N. Anal. Chem. 2005, 77, 4282.
Matsui, J.; Akamatsu, K.; Nishiguchi, S.; Miyoshi, D.; Nawafune, H.; Tamaki, K.; Sugimoto, N. Anal. Chem. 2004, 76, 1310.
Mosbach, K. Trends Biochem. Sci. 1994, 19, 9.
Obare, S. O.; Hollowell, R. E.; Murphy, C. J. Langmuir 2002, 18, 10407.
Phillips, K.S.; Cheng Q. Anal. Bioanl. Chem. 2007, 387, 1831.
Pinnaduwage, L.A.; Bioadjiev, V.; Hawk, J.E.; Thindat, T. Appl. Phys. Lett. 2003, 83, 1471.
Pogorelova, S. P.; Bourenko, T.; Kharitonov, A. B.; Willner,I. Analyst 2002, 127, 1484.
Pogorelova, S. P.; Zayats, M.; Bourenko, T.; Kharitonov, A. B.; Lioubashevski, O.; Katz, E.; Willner. I. Anal. Chem. 2003, 75, 509.
Politzer, P.; Ma, Y. Int. J. Quantum Chem. 2004, 100, 733.
Rice, B.M.; Chabalowski, C.F. J. Phys. Chem. A 1997, 101, 8720.
Riskin, M.; Tel-Vered, R.; Bourenko, T.; Granot, E.; Willner. I. J. Am. Chem. Soc. 2008, 130, 9726.
Rosi, N. L.; Mirkin, C. A. Chem. Rev. 2005, 105, 1547.
Shankaran, D. R.; Gobi, K. V.; Sakai, T.; Matsumoto, K.; Toko, K.; Miura, N. Biosens. Bioelectron. 2005, 20, 1750.
Shankaran, D.R.; Kawaguchi, T.; Kim, S.J.; Matsumoto, K.; Toko, K.; Miura, N. Anal. Bioanal. Chem. 2006, 386, 1313.
Shipway, A. N.; Lahav, M.; Blonder, R.; Willner, I. Chem. Mater. 1999, 11, 13.
Shipway, A. N.; Lahav, M.; Willner, I. AdV. Mater. 2000, 12, 993.
Shishkov, I.F.; El'fimova, T.L.; Vilov, L.V. J. Struct. Chem. 1992, 33, 41.
Shoji, R.; Takeuchi, T.; Kubo, I. Anal. Chem. 2003, 75, 4882.
Sohn, H.; Caldoun, R.M.; Sailor, M.J.; Trogler W.C. Angew. Chem. Int. Ed. 2001, 40, 2104.
Sohn, H.; Sailor, M. J.; Magde, D.; Trogler, W. C. J. Am. Chem. Soc. 2003, 125, 3821.
Storhoff, J. J.; Elghanian, R.; Mucic, R. C.; Mirkin, C. A.; Letsinger, R. L. J. Am. Chem. Soc. 1998, 120, 1959.
Suarez-Rodriguez, J. L.; Diaz-Garcia, M. E. Biosens. Bioelectron. 2001, 16, 955.
Surugiu, I.; Svitel, J.; Ye, L.; Haupt, K.; Danielsson, B. Anal. Chem. 2001, 73, 4388.
Swager, T. M. Acc. Chem. Res. 1998, 31, 201.
Toal, S. J.; Magde, D.; Trogler, W. C. Chem. Commun. 2005, 5465.
Toal, S.J.; Trogler, W.C. J. Mater. Chem. 2006, 16, 2871.
Tokareva, I.; Tokarev, I.; Minko, S.; Hutter, E.; Fendler, J. H. Chem. Commun. 2006, 31, 3343.
Wang, J.; Bhada, R. K.; Lu, J.; MacDonald, D. Anal. Chim. Acta 1998, 361, 85-91.
Wang, J.; Hocevar, S. B.; Ogorevc, B. Electrochem. Commun. 2004, 6, 176.
Wang, J.; Lu, F.; MacDonald, D.; Lu, J.; Ozsoz, M.E.S.; Rogers, K.R. Talanta 1998, 46, 1405.
Wang, J.; Thongngamdee, S.; Lu, D. Electroanalysis 2006, 18, 971.
Wang, W.; Gao, S.; Wang, B. Org. Lett. 1999, 1, 1209.
Weng, C.-H.; Yeh, W.-M.; Ho, K.-C.; Lee, G.-B. Sens. Actuators, B 2007, 121, 576.
Whelan, J.P.; Kusterbeck, A.W.; Wemhoff, G.A.; Bredehorst, R.; Ligler, F.S. Anal. Chem. 1993, 65, 3561.
Wulff, G. Angew. Chem., Int. Ed. 1995, 34, 1812.
Wulff, G. Chem. ReV. 2002, 102, 1.
Yang, J.-S.; Swager, T. M. J. Am. Chem. Soc. 1998, 120, 11864.
Yang, J.S.; Swager, T.M. J. Am. Chem. Soc. 1998, 120, 5321.
Yang, X.; Du, X.X.; Shi, J.; Swanson, B. Talanta 2001, 54, 439.
Zayats, M.; Lahav, M.; Kharitonov, A. B.; Willner, I. Tetrahedron 2002, 58, 815.
Zayats, M.; Pogorelova, S.P.; Kharitonov, A.B.; Lioubashevski. O.; Katz, E.; Willner, I. Chem. Eur. J. 2003, 9, 6108.
Zhang, H.-X.; Cao, A.-M.; Hu, J.-S.; Wan, L.-J.; Lee, S.-T. Anal. Chem. 2006, 78, 1967.
Zhang, H.-X.; Hu, J.-S.;Yan, C.-J.; Jiang, L.; Wan, L.-J. Phys. Chem. Chem. Phys. 2006, 8, 3567.
Zhou, Y.; Yu, B.; Shiu, E.; Levon. K. Anal. Chem. 2004, 76, 2689.
Matsunaga, T.; Hishiya, T.; Takeuchi, T. Anal. Chim. Acta 2007, 591, 63.
McGill, R.A.; Mlsna, T.E.; Chung, R.; Nguyen, V.K.; Stepnowski, J. Sens. Actuators, B 2000, 65, 5.
McQuade, D. T.; Pullen, A. E.; Swager, T. M. Chem. ReV. 2000, 100, 2537.
Riskin, M.; Tel-Vered, R.; Lioubashevski, O.; Willner, I. J. Amer. Chem. Soc. 2009, 131, 7368.
Riskin et al, Imprinted Au-Nanoparticle Composites . . . , Advanced Materials, vol. 22, Jan. 13, 2010, p. 1387-1391.
International Preliminary Report on Patentability for PCT/2020/1033 dated Jun. 12, 2012.
International Search Report for PCT/2010/1033 dated Jun. 1, 2011.

METHOD AND DEVICE FOR DETECTION OF NITROAMINES

FIELD OF THE INVENTION

This invention relates to a method and device for detecting nitroamines.

BACKGROUND OF THE INVENTION

Sensors for the detection of explosives are important for various disciplines including humanitarian de-mining, remediation of explosives waste sites, homeland security, and forensic applications. Different sensors for analyzing explosives were reported in the past decade. These included optical sensors where the fluorescence of functional polymers was quenched by the nitroaromatic compounds [1,2] luminescent polymer nanoparticles, such as polysilole, that were quenched by trinitrotoluene (TNT) [3] or fluorescent silicon nanoparticles that were quenched by nitroaromatic vapors [4].

The detection of more hazardous explosives such as hexahydro-1,3,5-trinitro-1,3,5-trizine (RDX) or pentaerythritol tetranitrate (PETN) is significantly less developed, and of need of further efforts, particularly the improvement of the sensitivities associated with the analysis of these substrates [5,6]. Different optical, electrochemical, or microgravimetric sensors or biosensors for TNT were reported. Fluorescent organic polymers which are quenched by nitroaromatic explosives [7,8], luminescent polysilole nanoparticles [9,10], or fluorescent silicon nanoparticles quenched by nitroaromatic vapors enabled the development of optical sensors. The electrochemical activity of the nitro groups of TNT, for example, provided the basis of developing voltammetric sensors for this explosive [11,12], and recently, a composite of gold nanoparticles linked to electrodes enabled a sensitive electrochemical detection of TNT [13].

The redox activity of the nitro groups associated with many of the explosives was used to develop electrochemical sensors [14], and modified electrodes such as mesoporous $SiO_2$-functionalized electrodes were employed to enhance the sensitivity of detection of nitroaromatic explosives [15]. Other electronic devices for the analysis of explosives included surface acoustic wave (SAW) systems. The coating of the piezoelectric devices with silicon polymers [16], carbowax [17] or cyclodextrin polymers [18] yielded functional coatings that enabled the electronic transduction of explosives adsorbed to these matrices; while the aggregation of functionalized gold nanoparticles in the presence of TNT was used to develop an optical sensor for the explosive [19].

The eliciting of antibodies that exhibit specific binding to nitroaromatics enabled the development of biosensors for explosives, using immunocomplexes as sensing units. This was exemplified with the development of TNT biosensors based on the displacement of the anti-TNT antibody from a surface-confined immunocomplex by TNT and the transduction of the dissociation of the antibody by surface plasmon resonance (SPR) spectroscopy [20-24] or quartz crystal microbalance (QCM) measurements [25]. Different optical [26,27] or voltammetric [28] sensors for RDX were also reported. These include the fluorescence detection of RDX with an acridinium dye [26], or by the application of NADH-functionalized quantum dots [29]. Also, a competitive fluorescence immunoassay for the detection of RDX was reported [30].

Although substantial progress was achieved in the sensing of explosives, the different analytical protocols suffer from insufficient sensitivity, lack of specificity, long analysis time intervals, and/or complex and expensive analytical protocols.

The unique electronic and optical properties of metallic and semiconductor nanoparticles, NPs, added new dimensions to the area of sensors. The aggregation of Au (gold) NPs as a result of sensing events and the formation of an interparticle coupled plasmon absorbance was used for the development of colorimetric sensors [31]. For example, color changes as a result of aggregation of Au nanoparticles were used to detect phosphatase activity [32], polynucleotides [33], or alkali (lithium) [34] ions. Also, the shifts in the plasmonic absorption bands associated with Au nanoclusters as a result of changes in the surface dielectric properties upon sensing were used to develop optical sensors for dopamine [35], adrenaline [36], cholesterol [37], DNA hybridization [38], and pH changes [39]. The layer-by-layer deposition of Au NPs on electrodes by the electrostatic cross-linking of the NPs by charged molecular receptors was used to construct electrochemical sensors for different neurotransmitters [40].

The imprinting of molecular recognition in organic or inorganic polymer matrices is known to permit generation of selective binding sites for the imprinted substrates [41]. Indeed, numerous optical [42] or electronic [43] sensors based on imprinted polymer matrices have been developed in the past two decades. For example, electrochemical sensors that consisted of imprinted organic [44] or inorganic [45] polymers were developed, and imprinted inorganic matrices associated with the gate surface of field-effect transistors were applied for the stereoselective or chiroselective analysis of the imprinted substrates [46]. Similarly, a quartz crystal microbalance [47] and surface plasmon resonance spectroscopy [48] were used as readout methods for the binding of substrates to the imprinted sites. The use of imprinted polymers as functional sensing matrices suffers, however, from several basic limitations. The density of imprinted sites is relatively low, and thus, for sensitive sensing thick polymer matrices are required. This leads, however, to slow binding of the analytes to the recognition sites (long analysis time intervals) and to an inefficient communication between the binding sites and the transducers. In fact, several studies suggested the use of imprinted monolayers [47], multilayers [48] and thin films to overcome these difficulties.

REFERENCES

[1] (a) Swager, T. M. *Acc. Chem. Res.* 1998, 31, 201. (b) McQuade, D. T.; Pullen, A. E.; Swager, T. M. *Chem. ReV.* 2000, 100, 2537. (c) Yang, J.-S.; Swager, T. M. *J. Am. Chem. Soc.* 1998, 120, 11864

[2] (a) Chang, C.-P.; Chao, C.-Y.; Huang, J.-H.; Li, A.-K.; Hsu, C.-S.; Lin, M.-S.; Hsieh, B.-R.; Su, A.-C. *Synth. Met.* 2004, 144, 297. (b) Sohn, H.; Sailor, M. J.; Magde, D.; Trogler, W. C. *J. Am. Chem. Soc.* 2003, 125, 3821

[3] (a) Chen, J.; Law, C. C. W.; Lam, J. W. Y.; Dong, Y.; Lo, S. M. F.; Williams, I. D.; Zhu, D.; Tang, B. Z. *Chem. Mater.* 2003, 15, 1535. (b) Toal, S. J.; Magde, D.; Trogler, W. C. *Chem. Commun.* 2005, 5465

[4] Content, S.; Trogler, W. C.; Sailor, M. J. *Chem. sEur. J.* 2000, 6, 2205

[5] Krause, A. R.; Van Neste, C.; Senesac, T.; Thundat, E.; Finot, E. *J. Appl. Phys.* 2008, 103, 094906

[6] Pinnaduwage, L. A.; Boiadjiev, V.; Hawk, J. E.; Thindat, T. *Appl. Phys. Lett.* 2003, 83, 1471

[7] Toal, S. J.; Trogler, W. C. *J. Mater. Chem.* 2006, 16, 2871

[8] Yang, J. S.; Swager, T. M. *J. Am. Chem. Soc.* 1998, 120, 5321

[9] Sohn, H.; Caldoun, R. M.; Sailor, M. J.; Trogler W. C. *Angew. Chem. Int. Ed.* 2001, 40, 2104

[10] Gao, D.; Wang, Z.; Liu, B.; Ni, L.; Wu, M.; Zhang, Z. *Anal. Chem.* 2008, 80, 8545

[11] Wang, J.; Bhada, R. K.; Lu, J.; MacDonald, D. *Anal. Chim. Acta* 1998, 361, 85-91

[12] Wang, J.; Lu, F.; MacDonald, D.; Lu, J.; Ozsoz, M. E. S.; Rogers, K. R. *Talanta* 1998, 46, 1405

[13] Riskin, M.; Tel-Vered, R.; Bourenko, T.; Granot, E.; Winner, I. *J. Am. Chem. Soc.* 2008, 130, 9726

[14] (a) Wang, J.; Hocevar, S. B.; Ogorevc, B. *Electrochem. Commun.* 2004, 6, 176. (b) Hrapovic, S.; Majid, E.; Liu, Y.; Male, K.; Luong, J. H. T. *Anal. Chem.* 2006, 78, 5504. (c) Zhang, H.-X.; Hu, J.-S.; Yan, C.-J.; Jiang, L.; Wan, L.-J. *Phys. Chem. Chem. Phys.* 2006, 8, 3567

[15] Zhang, H.-X.; Cao, A.-M.; Hu, J.-S.; Wan, L.-J.; Lee, S.-T. *Anal. Chem.* 2006, 78, 1967

[16] McGill, R. A.; Mlsna, T. E.; Chung, R.; Nguyen, V. K.; Stepnowski, J. *Sens. Actuators, B* 2000, 65, 5

[17] Yang, X.; Du, X. X.; Shi, J.; Swanson, B. *Talanta* 2001, 54, 439

[18] Kalman, G. K.; Nimal, A. T.; Mittal, U.; Yadava, R. D. S.; Kapoor, J. C. *Sens. Actuators, B* 2004, 101, 328

[19] Jiang, Y.; Zhao, H.; Zhu, N.; Lin, Y.; Yu, P.; Mao, L. *Angew. Chem. Int. Ed.* 2009, 47, 8601

[20] Larsson, A.; Angbrant, J.; Ekeroth, J.; Mansson, P.; Liedberg, B. *Sens. Actuators, B* 2006, 113, 730

[21] Shankaran, D. R.; Gobi, K. V.; Sakai, T.; Matsumoto, K.; Toko, K.; Miura, N. *Biosens. Bioelectron.* 2005, 20, 1750

[22] Bromage, E. S.; Lackie, T.; Unger, M. A.; Ye, J.; Kaattari, S. L. *Biosens. & Bioelectron.* 2007, 22, 2532

[23] Whelan, J. P.; Kusterbeck, A. W.; Wemhoff, G. A.; Bredehorst, R.; Ligler, F. S. *Anal. Chem.* 1993, 65, 3561

[24] Shankaran, D. R.; Kawaguchi, T.; Kim, S. J.; Matsumoto, K.; Toko, K.; Miura, N. *Anal. Bioanal. Chem.* 2006, 386, 1313

[25] Cerruti, M.; Jaworski, J.; Raorane, D.; Zueger, C.; Varadarajan, J.; Carraro, C.; Lee, S. W.; Mabuodian, R.; Majumdar, A. *Anal. Chem.* 2009, 81, 4192

[26] Andrew, T. L.; Swager, T. M. *J. Am. Chem. Soc.* 2007, 129, 7254

[27] Bart, J. C.; Judd, L. L.; Kusterbeck, A. W. *Sens. Actuators, B* 1997, 39, 411

[28]. Wang, J.; Thongngamdee, S.; Lu, D. *Electroanalysis* 2006, 18, 971

[29] Freeman, R.; Willner, I. *Nano Lett.* 2009, 89, 322

[30] Bakaltcheva, L B.; Ligler, F. S., Patterson, C. H.; Shriver-Lake, L. C. *Anal. Chim. Acta* 1999, 399, 13

[31] (a) Daniel, M.-C.; Astruc, D. *Chem. ReV.* 2004, 104, 293. (b) Rosi, N. L.; Mirkin, C. A. *Chem. Rev.* 2005, 105, 1547

[32] Choi, Y.; Ho, N.-H.; Tung, C.-H. *Angew. Chem., Int. Ed.* 2007, 46, 707

[33] Storhoff, J. J.; Elghanian, R.; Mucic, R. C.; Mirkin, C. A.; Letsinger, R. L. *J. Am. Chem. Soc.* 1998, 120, 1959

[34] Obare, S. O.; Hollowell, R. E.; Murphy, C. J. *Langmuir* 2002, 18, 10407

[35] Matsui, J.; Akamatsu, K.; Hara, N.; Miyoshi, D.; Nawafune, H.; Tamaki, K.; Sugimoto, N. *Anal. Chem.* 2005, 77, 4282

[36] Matsui, J.; Akamatsu, K.; Nishiguchi, S.; Miyoshi, D.; Nawafune, H.; Tamaki, K.; Sugimoto, N. *Anal. Chem.* 2004, 76, 1310

[37] Tokareva, I.; Tokarev, I.; Minko, S.; Hutter, E.; Fendler, J. H. *Chem. Commun.* 2006, 31, 3343

[38] Hu, W. P.; Chen, S.-J.; Huang, K.-T.; Hsu, J. H.; Chen, W. Y.; Chang, G. L.; Lai, K.-A. *Biosens. Bioelectron.* 2004, 19, 1465

[39] Jiang, G.; Baba, A.; Ikarashi, H.; Xu, R.; Locklin, J.; Kashif, K. R.; Shinbo, K.; Kato, K.; Kaneko, F.; Advincula, R. *J. Phys. Chem. C* 2007, 111, 18687

[40] (a) Shipway, A. N.; Lahav, M.; Willner, I. *AdV. Mater.* 2000, 12, 993. (b) Lahav, M.; Gabai, R.; Shipway, A. N.; Willner, I. *Chem. Commun.* 1999, 19, 1937. (c) Shipway, A. N.; Lahav, M.; Blonder, R.; Willner, I. *Chem. Mater.* 1999, 11, 13. (d) Lahav, M.; Shipway, A. N.; Willner, I.; Nielsen, M. B.; Stoddart, J. F. *J. Electroanal. Chem.* 2000, 482, 217

[41] (a) Wulff, G. *Angew. Chem., Int. Ed.* 1995, 34, 1812. (b) Wulff, G. *Chem. ReV.* 2002, 102, 1. (c) Mosbach, K. *Trends Biochem. Sci.* 1994, 19, 9. (d) Haupt, K.; Mosbach, K. *Chem. ReV.* 2000, 100, 2495. (e) Bossi, A.; Bonini, F.; Turner, A. P. F.; Piletsky, S. A. *Biosens. Bioelectron.* 2007, 22, 1131

[42] (a) Suarez-Rodriguez, J. L.; Diaz-Garcia, M. E. *Biosens. Bioelectron.* 2001, 16, 955. (b) Surugiu, I.; Svitel, J.; Ye, L.; Haupt, K.; Danielsson, B. *Anal. Chem.* 2001, 73, 4388. (c) Wang, W.; Gao, S.; Wang, B. *Org. Lett.* 1999, 1, 1209. (d) Hu, X.; An, Q.; Li, G.; Tao, S.; Liu, J. *Angew. Chem., Int. Ed.* 2006, 45, 8145

[43] (a) Liang, H.-J.; Ling, T.-R.; Rick, J. F.; Chou, T.-C. *Anal. Chim. Acta* 2005, 542, 83. (b) Kirsch, N.; Hart, J. P.; Bird, D. J.; Luxton, R. W.; McCalley, D. V. *Analyst* 2001, 126, 1936

[44] (a) Weng, C.-H.; Yeh, W.-M.; Ho, K.-C.; Lee, G.-B. *Sens. Actuators, B* 2007, 121, 576. (b) Shoji, R.; Takeuchi, T.; Kubo, I. *Anal. Chem.* 2003, 75, 4882

[45] (a) Zhou, Y.; Yu, B.; Shiu, E.; Levon, K. *Anal. Chem.* 2004, 76, 2689. (b) Fireman-Shoresh, S.; Turyan, I.; Mandler, D.; Avnir, D.; Marx, S. *Langmuir* 2005, 21, 7842. (c) Lahav, M.; Kharitonov, A. B.; Katz, O.; Kunitake, T.; Willner, I. *Anal. Chem.* 2001, 73, 720

[46] (a) Zayats, M.; Lahav, M.; Kharitonov, A. B.; Willner, I. *Tetrahedron* 2002, 58, 815. (b) Pogorelova, S. P.; Zayats, M.; Bourenko, T.; Kharitonov, A. B.; Lioubashevski, O.; Katz, E.; Willner, I. *Anal. Chem.* 2003, 75, 509

[47] (a) Pogorelova, S. P.; Bourenko, T.; Kharitonov, A. B.; Willner, I. *Analyst* 2002, 127, 1484. (b) Cao, L.; Li, S. F. Y.; Zhou, X. C. *Analyst* 2001, 126, 184

[48] (a) Matsunaga, T.; Hishiya, T.; Takeuchi, T. *Anal. Chim. Acta* 2007, 591, 63. (b) Li, X.; Husson, S. M. *Biosens. Bioelectron.* 2006, 22, 336. (c) Raitman, O. A.; Chegel, V. I.; Kharitonov, A. B.; Zayats, M.; Katz, E.; Willner, I. *Anal. Chim. Acta* 2004, 504, 101

[49] Knoll, W. *Annu. Rev. Phys. Chem.* 1998, 49, 569

[50] Phillips, K. S.; Cheng Q. *Anal. Bioanl. Chem.* 2007, 387, 1831

[51] Gordon, R.; Sinton, D.; Kavanagh, K. L.; Brolo, A. G. *acc. Chem. Res.* 2008, 41, 1049

[52] Homola, J. *Cehm. Rev.* 2008, 108, 462

[53] Berger, C. E. H.; Beumer, T. A. M.; Kooyman, R. P. H.; Greve, J. *Anal. Chem.* 1998, 70, 703

[54] Lyon, L. A.; Musick, M. D.; Smith, P. C.; Reiss, B. D.; Pena, D. J.; Natan, M. J. *Sens. Actuators, B* 1999, 54, 118

[55] Agarwal, G. S., Sutta Gupta, S. *Phys. Rev. B* 1985, 32, 3607

[56] He, L.; Musick, M. D.; Nicewarner, S. R.; Sallinas, F. G., Benkovic, S. J.; Natan, M. J.; Keating, C. D. *J. Am. Chem. Soc.* 2000, 122, 9071

[57] Lyon, L. A.; Musick, M. D., Natan M. *J. Anal. Chem.* 1998, 70, 5177

[58] Zayats, M.; Pogorelova, S. P.; Kharitonov, A. B.; Lioubashevski, O.; Katz, E.; Willner, I. *Chem. Eur. J.* 2003, 9, 6108

[59] Riskin, M.; Tel-Vered, R.; Lioubashevski, O.; Willner, I. *J. Amer. Chem. Soc.* 2009, 131, 7368

[60] Doron, A.; Katz, E.; Willner, I. *Langmuir* 1995, 11, 1313

[61] Wulff, G. *Chem. Rev.* 2002, 102, 1

[62] Haupt, K.; Mosbach, K. *Chem. Rev.* 2000, 100, 2495

[63] Bossi, A.; Bonini, F.; Turner, A. P. F.; Piletsky, S. A. *Biosens. & Bioelectron.* 2007, 22, 1131

[64] Haupt, K. *Analyst,* 2001, 126, 747

[65] Shishkov, I. F.; El'fimova, T. L.; Vilkov, L. V. *J. Struct. Chem.* 1992, 33, 41

[66] Rice, B. M.; Chabalowski, C. F. *J. Phys. Chem. A* 1997, 101, 8720

[67] Politzer, P.; Ma, Y. *Int. J. Quantum Chem.* 2004, 100, 733

SUMMARY OF THE INVENTION

The present invention, in most general terms, provides use of nanoparticle matrices for ultra sensitive and selective detection of non-aromatic, and structurally non-planar nitroamine analyte molecules such as hexahydro-1,3,5-trinitro-1,3,5-triazine (RDX) and other nitroamine compounds.

In one aspect of the invention, there is provided a method for determining the presence and/or concentration of non-aromatic non-planar nitroamine analyte molecules in a sample, said method comprising contacting a matrix of a plurality of transition metal nanoparticles (TMNPs), each carrying a plurality of recognition groups, with a sample suspected of containing non-aromatic nitroamine analyte molecules, and monitoring at least one of a chemical and a physical change in said matrix, i.e., resulting from an interaction between said non-aromatic nitroamine analyte molecules and said matrix, via the recognition groups, wherein said at least one of a chemical and a physical change is indicative of at least one of presence and quantity of said non-aromatic nitroamine analyte (such as RDX or any other nitroamine compound or combination thereof) in the sample.

The matrix is composed of TMNPs associated with each other through a plurality of recognition groups being carried on their surface. As each nanoparticle may form more than one bond with a neighboring nanoparticle, as further disclosed below, a net is formed having a multitude of analyte-recognition fields (in the form of cavities) that are complementary in shape and/or size to the non-aromatic nitroamine analyte molecules to be detected. Typically, the matrix is a three-dimensional structure. As the non-aromatic nitroamine analytes to be detected, such as RDX, WAX and others are known to adopt a non-planar conformation (one or more such conformations may be envisaged for the main ring structure), the three-dimensional structure which forms may be distinct to each of the analytes and thus may be of greater selectively to each analyte in comparison to other methods of analyte detection, as further demonstrated hereinbelow.

The analyte-recognition fields constitute cavities within the matrix, suitable for holding/binding the analyte molecules therein, thereby permitting at least one interaction between the analyte molecules and the recognition groups. The analyte-recognition fields may be of any size and shape. The plurality of TMNPs in the matrix are associated with each other through a plurality of recognition groups, each group linking at least two TMNPs, thereby forming the boundaries of the analyte-recognition fields in the matrix.

The groups linking the TMNPs are referred to as "recognition groups" for having the ability to chemically and/or physically interact with the analyte molecules (RDX or other nitroamine compounds), thereby ensuing their recognition. The recognition groups are so selected to permit recognition of a single molecular shape and/or size, a family of compounds having a distinct shape or chemical constitution (e.g., having triazine or tetrazine groups, or nitro groups or a combination thereof), or a class of compounds identified by their ability to undergo chemical interaction (i.e., chemical reaction) when in the matrix. Thus, the purpose of the recognition groups is not only to provide a net having a plurality of analyte-recognition fields around the TMNPs, but also permit interaction (reversible or permanent) with the analyte molecules which enter the analyte-recognition fields, as further disclosed below.

The recognition groups are selected to undergo chemical and/or physical interaction with the analyte molecules (one or more) present in the analyte-recognition fields. Such an interaction may be through a single, double or triple bond, or through one or more of van der Waals, hydrogen bonding, electrostatic interaction, complexation, caging and other physical interactions as known in the art. In some embodiments, the physical interaction is reversible.

In some embodiments, the recognition groups are selected to have certain length and substitution so as to predefine the shape and size of the non-planar analyte-recognition fields formed between the TMNPs. Typically, the longer the recognition groups are (or the less compact the analyte conformation is), the bigger the fields which are formed; the more substituted the recognition groups are, the denser or more crowded the fields are.

The recognition groups are typically selected to maintain strong and, in some embodiments, permanent (irreversible) interaction (association, bonding) with the TMNPs. Such association is dependent on the nature of the TMNPs, their size and to a lesser extent, in some embodiments, also on the method employed for achieving association between the TMNPs and the recognition groups. In some embodiments, the recognition groups are residues of "electropolymerizable groups", namely groups which association (e.g., covalent bonding) with the TMNPs is achieved, at least partially, through electropolymerization.

The TMNPs are nanoparticles of at least one transition metal selected from the d-block of the Periodic Table of the Elements. In some embodiments, nanoparticles are of a metal selected from platinum (Pt), palladium (Pd), iridium (Ir), gold (Au), silver (Ag), nickel (Ni) and titanium (Ti), or alloys thereof. In some embodiments, the TMNPs are gold nanoparticles. In some embodiments, the TMNPs contain gold metal and at least one additional transition metal, at least one non-metal or at least one metal (not a transition metal).

The TMNPs forming the matrix may be a mixture of two or more nanoparticle types, each may be of a different metal or metal alloy, different size, different shape, etc. In some embodiments, the matrix is composed of a mixture of gold nanoparticles and other metallic particles. In other embodiments, the matrix is composed of nanoparticles of various metals. In still other embodiments, the matrix is composed solely of gold nanoparticles.

The TMNPs may be of any shape, such as spherical, elongated, cylindrical, or in the form of amorphous nanoparticles. The TMNPs typically have at least one dimension (diameter, width) in the range of about 1 nm to 1000 nm. In some embodiments, each TMNP is, on average, of a nanometer scale (size), ranging between 1 nanometer to 1000 nanometer; between 1 nanometer and 500 nanometers; between 1 nanometer and 250 nanometers; between 1 nanometer and 250 nanometers; between 1 nanometer and 150 nanometers; between 1 nanometer and 100 nanometers; between 1 nanometer and 50 nanometers; between 1 nanometer and 25 nanometers; between 1 nanometer and 10 nanometers and between 1 nanometer and 5 nanometers. In some further embodiments, each TMNP is, on average, 1, 2, 3, 4, 5, 6, 7, 8, 9, 10 nanometers in diameter, or any intermediate diameter, e.g., 1.1, 1.2, 1.3 . . . 2.1, 2.2, 2.3 . . . 3.1, 3.2, 3.3 . . . etc.

As stated above, the matrix comprises a plurality of TMNPs, each being associated with one another through one or more recognition moieties. Such recognition moieties may have one or more reactive groups which are capable of undergoing interaction with the nanoparticles. Non-limiting examples of such reactive groups are —S, —$NH_2$ and —$CO_2^-$. In some embodiments, where the matrix comprises or is entirely composed of gold nanoparticles, the recognition groups may be selected to have one or more reactive groups which are capable of undergoing interaction with the gold nanoparticles. In such embodiments, the one or more reactive groups are sulfur containing groups, particularly thiols. In some embodiments, the thiols are selected amongst aromatic thiols or alkyl thiols having at least one aromatic substituent. Non-limiting examples of such sulfur containing recognition groups are thioaniline, thioaniline dimer and oligomers thereof.

In some embodiments, the recognition groups having one or more sulfur-containing groups are selected from p-thioaniline and the oligo-thioanilines having 2, 3, 4, 5, 6, 7, 8, 9 or 10 p-thioaniline monomer units. In further embodiments, the recognition groups are electorpolymerized thioanilines. In some embodiments, the recognition groups is the thioaniline dimer 4-amino-3-(4-mercaptophenylamino) benzenthiol, i.e., wherein the terminal —S-aryl groups undergo association with the gold nanoparticles.

It should be noted that each TMNP may further be functionalized to affect a change (increase, decrease or substantially maintain an intrinsic property of the nanoparticle) in one or more property associated with the nanoparticles, such property may be physical or chemical and may be selected from solubility, film forming properties, aggregation, reactivity, stickiness, stabilization, reusability, adhesion, charge, interaction with a medium, and other known properties. In some embodiments, the TMNPs are functionalized to increase their solubility in a liquid medium, e.g., an aqueous medium. In other embodiments, the TMNPs are functionalized to increase their shelf-life and reusability in the matrix of the invention. In some further embodiments, the TMNPs are functionalized with negatively or positively charged functional groups. In additional embodiments, the TMNPs are functionalized with sulfonic acid containing groups. A non-limiting example of a sulfonic acid group is 2-mercaptoethane sulfonic acid or an anion thereof.

In some additional embodiments, the TMNPs are functionalized with monomers of the recognition groups which have not undergone polymerization and subsequent association with neighboring TMNPs.

In some embodiments, the TMNP matrix is bound to an active surface which, in some embodiments, is conductive and thus capable of reporting at least one chemical and/or physical change resulting from an interaction between the TMNP matrix and the analyte molecules in the sample. The active surface may be a metal body or a metallic surface of a metal selected from gold, platinum, silver, and alloys thereof. In some embodiments, the active surface is a non-metallic body, such as graphite, Indium-Tin-Oxide (ITO), glass and others, which may or may not be coated with a metallic coating.

In some embodiments, the active surface is an electrode. In other embodiments, the active surface is a metal (or alloy) coated glass.

The active surface may be a two-dimensional surface on top of which the matrix is formed or may be a three-dimensional body having, e.g., a circumference which is fully or partially associated with the matrix. In some embodiments, the matrix completely covers the active surface. In other embodiments, the matrix is formed on spaced-apart regions of the active surface.

In some embodiments, the matrix is associated with said active surface through one or more surface-binding moieties. The surface-binding moieties may or may not be the same as the recognition groups used to associate the plurality of TMNP in the matrix. In some embodiments, where the active surface is a gold surface and the TMNPs are gold nanoparticles, the surface-binding moieties and the recognition groups compose sulfur containing groups, such as thiols, as further disclosed hereinabove. In further embodiments, the surface-binding moieties and the recognition groups are p-thioaniline or a dimer or oligomer thereof.

In order to associate the matrix with the active surface, it is not necessary to have all nanoparticles of the matrix associated with the surface. It is merely required that a portion of the matrix is associated with the surface through the surface-binding groups.

It should be noted, that in embodiments where electropolymerization is employed for the construction of the matrix, the matrix may contain elecotropolymerized recognition groups and electropolymerized surface-binding groups of various lengths (a varying number of monomers, e.g., p-thioaniline monomers). For example, the matrix may be composed of nanoparticles which are associated with each other via dimers of p-thioaniline and nanoparticles which are associated via a different oligomer, e.g., trimer, quartermer, etc. Thus, in some embodiments, the matrix is inhomogeneous, i.e., not arranged from a single type of recognition group nor is it arranged in an ordered multilayered structure.

The non-aromatic nitroamine analyte molecules which may be detected, using a method according to the invention, are numerous. As used herein, the "non-aromatic, non-planar" analyte molecules are organic nitroamines which do not have one or more aromatic (benzene) ring as their main ring structure. Typically, the analytes detected according to the method of the invention are different from aromatic nitro compounds.

As the matrix, i.e., TMNPs and recognition groups may be tailored to assay the presence and/or quantity of a certain analyte in a sample, the method of the invention may be both generic and, as desired, analyte-specific. In some embodiments, the non-aromatic nitroamine analyte to be assayed is an organic material. In still other embodiments, the non-aromatic nitroamine analyte is selected from hexahydro-1,3, 5-trinitro-1,3,5-triazine (RDX), octahydro-1,3,5,7-tetranitro-1,3,5,7-tetrazocine (HMX), and 2,4,6,8,10,12-hexanitro-2,4,6,8,10,12-hexaazaisowurtzitane (CL-20). In some further embodiments, the analyte is RDX or HMX or a combination thereof.

The method of the invention may be carried out by bringing into contact the matrix comprising the TMNPs, as defined herein, with a sample (control or the so-called field-sample suspected of comprising the analyte) in such a way to permit interaction between the recognition groups of the matrix and the non-aromatic nitroamine analyte molecules. For achieving interaction, the matrix may be introduced into the sample (e.g., by dipping) for a period of time sufficient to achieve (not necessarily complete) interaction. The dipping may be repeated. Alternatively, the sample may be added onto the matrix (e.g., dripping). Other methods are suitable alternatives. Typically, the matrix and the sample are brought into contact at room temperature.

The interaction between the matrix, i.e., the recognition groups, and the analyte molecules, e.g., RDX molecules, may be probed by monitoring at least one measurable change, the change being associated with a change in at least one property or structure of the target molecule or one or more component of the matrix (or the matrix as a whole) caused by said interactions. Specifically, the measurable change may be, for example, in any one electric property or any one electrochemical property or any one spectroscopic property.

In some embodiments, the at least one change is in at least one electric property of the analyte and/or the matrix. The change may be measured by determining, e.g., current-voltage relationship, impedance, and other parameters, prior to and after the matrix and the sample have been brought into contact with each other. For quantitative measurements, calibration curves may be used.

In some other embodiments, the at least one change is in at least one optical property of the analyte and/or the matrix. Such optical property may be detected by Surface Plasmon Resonance (SPR), infra-red (IR) spectroscopy, Raman spectroscopy, X-ray photoelectron spectroscopy (XPS), photonic detection, evanescent detection, and cantilever detection.

In some embodiments, the qualitative and/or quantitative analysis of the non-aromatic nitroamine analyte is achieved by employing SPR to probe a change in a dielectric property of the analyte and/or the matrix or a combination thereof. In some embodiments, for SPR measurements, the active surface to which the matrix is bound is a gold-coated glass, e.g., an SPR cell (chip).

Thus, in some embodiments, the method of the invention comprises:

(a) providing nanoparticles of a transition metal, said nanoparticles carrying a plurality of recognition groups capable of undergoing interaction with non-aromatic nitroamine analyte molecules, e.g., RDX molecules;

(b) contacting said nanoparticles with a sample suspected of containing non-aromatic nitroamine analyte molecules;

(c) providing assay conditions to permit interaction between said recognition groups and the non-aromatic nitroamine analyte molecule(s), e.g., RDX molecules; and (d) probing the interaction to thereby detect at least one change in at least one dielectric property in the vicinity of the nanoparticles, whereby said change is indicative of at least the presence and quantity of said analyte molecule(s), e.g., RDX molecules, in the sample.

In another aspect the invention provides an electrode for carrying out the method of the invention. In some embodiments, the electrode has a conductive surface connected to a matrix, said matrix comprising a plurality of transition metal nanoparticles (TMNPs), wherein substantially each of said nanoparticles is connected to another by at least one recognition group capable of mediating electron transfer between nanoparticles of the matrix; at least a portion of said plurality of nanoparticles is connected to said conductive surface by at least one surface binding group, capable of mediating electron transfer between the matrix and said conductive surface.

In some embodiments, each of the TMNPs is selected as defined above.

In some embodiments, the matrix is produced by molecular imprinting.

Thus, the invention also provides a method for molecular imprinting of a matrix for detecting a non-aromatic nitroamine analyte, said method comprising:

modifying the surface of a solid support through the attachment of functional groups, e.g., the surface binding groups;

reacting, in the presence of at least one guest molecule, the functional groups of the modified solid support with transition metal nanoparticles carrying a plurality of recognition groups capable of undergoing interaction with non-aromatic nitroamine analyte molecules, under conditions allowing formation of a matrix embedded with said at least one guest molecule, wherein said matrix is thereby composed of a plurality of nanoparticles associated with each other through recognition groups; and removing said at least one guest molecule to thereby produce a molecularly-imprinted matrix on the solid substrate.

Without wishing to be bound by theory, the imprinting method increases, together with the complementary π-donor-acceptor interactions, the association of the non-aromatic nitroamine analyte molecules, e.g., RDX, to the sensing electrode (active surface of the solid support), thereby enhancing the sensitivity of the analysis.

In some embodiments, the at least one guest molecule is selected to have at least one of shape, size, substitution and electronic structure and distribution as that of the non-aromatic nitroamine analyte molecule, e.g., RDX, to be detected. In some embodiments, the at least one guest molecule is identical to the non-aromatic nitroamine analyte molecule, e.g., RDX. In some further embodiments, the at least one guest molecule has the same substituents and substituent pattern as the non-aromatic nitroamine analyte molecule. In further embodiments, the at least one guest molecule is larger in its overall space occupying volume than that of the analyte molecule. In additional embodiments, the at least one guest molecule is a mixture of two or more guest molecules, one of which may or may not be the same as the analyte molecule. For RDX detection, the guest molecule is selected from RDX, Kemp's acid, cis-1,3,5-tricarboxycyclohexane and cis-1,3-dicarboxycyclohexane.

For the purpose of employing the matrix thus formed for assaying the presence and/or quantity of a certain analyte molecule, the imprinting method of the invention provides for the removal of the guest molecule from the matrix, to thereby form the analyte-recognition fields. The at least one guest molecule may be removed from the matrix in the imprinting process by contacting, e.g., washing the matrix with a suitable solvent, such as an organic solvent or an aqueous solution at a desired pH. In some embodiments, the washing solution is an aqueous solution or a buffer at a substantially neutral pH (~6.5-7.5). In some embodiments, the buffer used has an acidic or basic pH.

In some embodiments, the method of imprinting further comprises the step of verifying the total removal of the guest molecules.

The method may further comprise the step of determining the base-line property of the matrix to be used in the calibration of the matrix or device. The base-line property is typically identical to the electric, electrochemical and/or optical property used to probe the change in the matrix after contact with the analyte sample. For example, if SPR measurements are used to assay the presence of RDX molecules in a sample, the dielectric properties of the matrix prior to coming in contact with the sample will be determined as the base-line property of the matrix.

In some embodiments, the solid support is an electrode or a coated glass slide (cell or chip). In some further embodiments, the glass cell is coated with gold.

In some embodiments, the matrix is formed by electropolymerization.

The matrix produced by the imprinting method of the invention, may be used in a method for detecting a non-aromatic nitroamine analyte, e.g., RDX, using the molecularly-imprinted matrix, the method comprising exposing the molecularly-imprinted matrix to a sample suspected of containing said analyte and detecting the interaction of the analyte, as disclosed herein, with the matrix. It should be noted, that while the present invention discloses an imprinting method for the production of the matrix, the matrix may be produced by any other process provided that it follows the definition and characteristics provided herein.

In some embodiments, the interaction (physical or chemical) is detected using electric or optical methods, e.g., SPR or voltammetric measurements.

In a further aspect there is provided a device for carrying out the detection of an analyte in a sample, said device comprising at least one assay unit having a plurality of nanoparticles of a transition metal, said nanoparticles carrying recognition groups capable of undergoing interaction with the analyte molecule(s), under predetermined assay conditions. The device may further comprise means to probe the interaction between said recognition groups and the analyte molecule(s) and means for detecting at least one change in at least one measurable property (electric or optical). In some embodiments, where the device is intended for electric measurements, the assay unit may comprise an electrode. For optical analysis, the assay unit may, for example, be in the form of an SPR cell or chip.

The invention also provides a sensor comprising an electrode according to the invention.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1A:
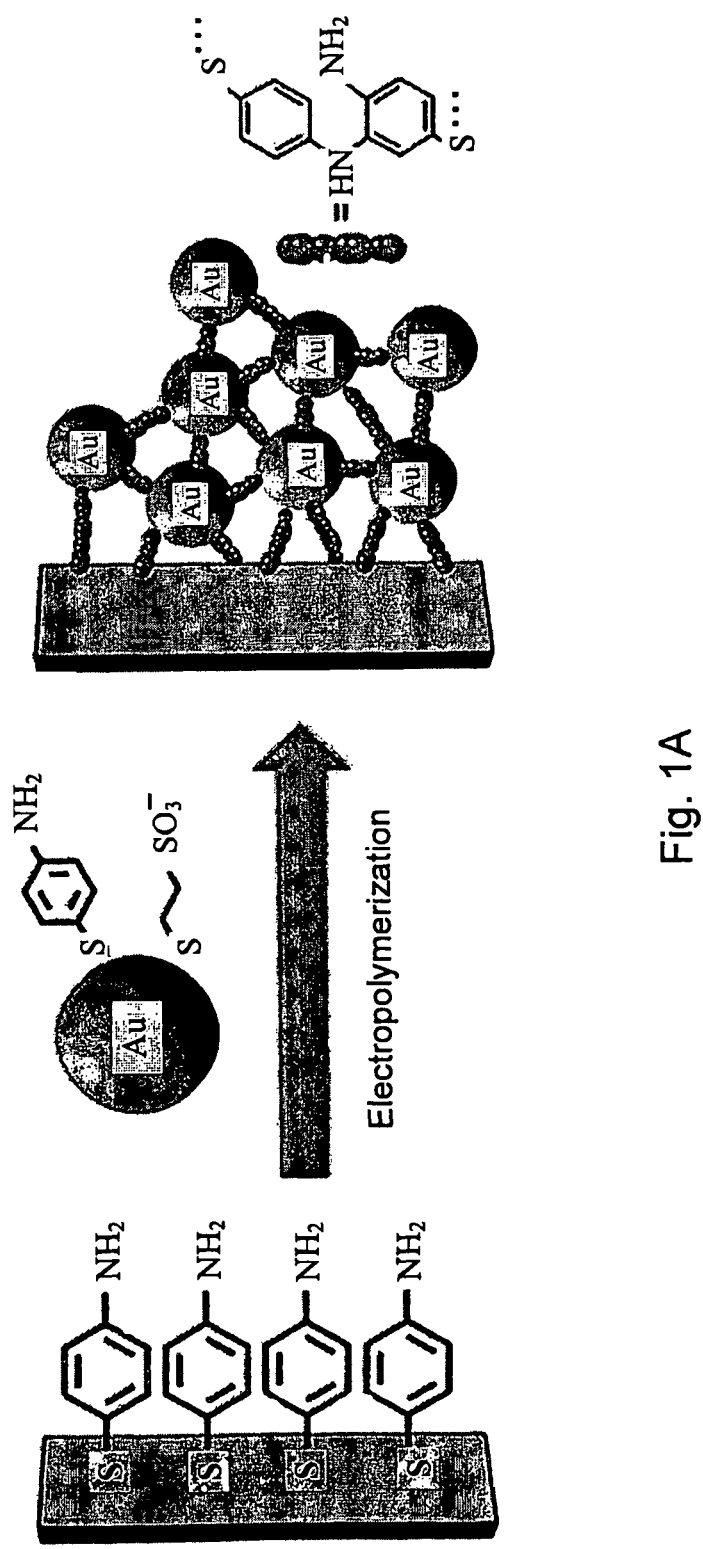
FIGS. 1A-1C are (A) Schematic presentation for the electropolymerization of a bis-aniline-crosslinked Au nanoparticles composite for the sensing of RDX by π-donor-receptor interactions. (B) SPR curves corresponding to the bis-aniline Au nanoparticles composite: (a) before the addition of RDX, and (b) after the addition of RDX, 20 nM. (C) Sensogram corresponding to the changes in the reflectance intensities, at a constant angel θ=63.3°, upon addition of variable concentrations of RDX: (a) 0 nM, (b) 4 nM, (c) 10 nM, (d) 20 nM, (e) 100 nM, (f) 500 nM, (g) 2 µM, (h) 10 µM. (D) calibration curve relating the reflectance changes to the concentration of RDX. All measurements were performed in a 0.1 M HEPES buffer solution, pH=7.2.

Electrochemical sensors for the analysis of RDX with enhanced sensitivities are herein disclosed. The enhanced sensitivities are achieved by tailoring π-donor-acceptor interactions between RDX and π-donor modified electrodes or π-donor-cross-linked Au nanoparticles linked to the electrode. In one configuration a p-aminothiophenolate monolayer-modified electrode leads to the analysis of RDX with a sensitivity corresponding to 12 fM. In the second configuration, the cross-linking of Au nanoparticles by oligothioaniline bridges to the electrode yields a functionalized electrode that detects RDX with a sensitivity that corresponds to 460 ppt (2 nM). Most impressively, the imprinting of molecular TNT recognition sites into the π-donor oligoaniline-cross-linked Au nanoparticles yields a functionalized electrode with a sensitivity that corresponds to 46 ppt (200 µM). The electrode reveals high selectivity, reusability, and stability.

Surface Plasmon Resonance

Surface Plasmon resonance (SPR) is a versatile method for probing changes in the refractive index occurring on thin films as a result of recognition vents or chemical reactions [50,51]. Numerous SPR sensors and biosensors were developed [52-54], and metal nanoparticles (NPs) were implemented to enhance the SPR response and to amplify SPR-based sensors [55,56]. The electronic coupling between the localized Plasmon of the metallic NPs (e.g., Au) and the surface plasmon wave enhances the SPR response, and thus, the labeling of a recognition complex with metallic NPs amplifies the sensing events. Different biosensing processes such as DNA hybridization [57], formation of immune-complexes [58], and the probing of biocatalytic transformations [59] used Au NPs as labels for amplified SPR analyses. Recently, bis-aniline-crosslinked Au NPs composites were electropolymerized om Au electrodes and the resulting matrices were used for the ultrasensitive SPR detection of TNT [60]. The formation of n-donor-acceptor complexes between TNT and the π-donor bis-aniline bridging units altered the dielectric properties of the Au NPs composites. This affected the coupling between the localized plasmon of the NPs and the surface plasmon wave, resulting in a shift in the surface resonance wave (i.e., reflectance changes), that enabled the optical readout for analyzing TNT. Theoretical modeling of the SPR shifts indicated that the charge transfer complexes between TNT and the bis-aniline bridging units altered the dielectric functions of the Au NPs composite, and this enabled the highly-sensitive detection of TNT [60].

Nanoparticles Synthesis

Gold nanoparticles functionalized with 2-mercaptoethane sulfonic acid and p-aminothiophenol (Au NPs) were prepared by mixing a 10 mL solution containing 197 mg of HAuC14 in ethanol and a 5 mL solution containing 42 mg of mercaptoethane sulfonate and 8 mg of p-aminothiophenol in methanol. The two solutions were stirred in the presence of 2.5 mL of glacial acetic acid in an ice bath for 1 hour. Subsequently, 7.5 mL of aqueous solution of 1 M sodium borohydride, $NaBH_4$, was added drop-wise, resulting in a dark colored solution associated with the presence of the Au NPs. The solution was stirred for 1 additional hour in an ice bath and then for 14 hours at room temperature. The particles were successively washed and centrifuged (twice in each solvent) with methanol, ethanol, and diethyl ether. An average particle size of 3.5 nm was estimated using Transmission Electron Microscopy (TEM). Nanopure (Barnstead) ultrapure water was used in the preparation of the different solutions.

Chemical Modification of the Electrodes

Au-coated semi-transparent glass plates (Mivitec GmbH, Analytical μ-Systems, Germany) were used as working electrodes. Prior to modification, the Au surface was cleaned in ethanol (at 50° C.) for 30 min. p-Aminothiophenol-functionalized electrodes were prepared by immersing the Au plates for 24 hours into a p-aminothiophenol ethanolic solution, 50 mM. The bis-aniline-crosslinked Au NPs-modified Au electrode was prepared by electropolymerization of the p-aminothiophenol-modified Au surface with the p-aminothiophenol-functionalized Au—NPs, 2 mg·mL$^{-1}$, in 0.1 M HEPES solution, pH=7.2. The electropolymerization was performed by the application of 10 potential cycles between −0.35 and 0.8 V vs. Ag quasi-reference electrode, at a potential scan rate of 100 mV s-1, followed by the application of a constant potential, E=0.8 V vs. Ag QRE for 30 minutes. The resulting films were washed with the background electrolyte solution to exclude any residual monomer from the electrode. Similarly, Kemp's acid, cis-1,3,5-tricarboxycyclohexane and cis-1,3-dicarboxycyclohexane-imprinted bis-aniline-crosslinked films were prepared by adding 10 mg·mL$^{-1}$ of the corresponding imprint analog molecule to the Au NPs mixture prior to the electropolymerization process. The extraction of the analog molecules from the film was carried out by immersing the electrodes in a 0.1 M HEPES solution, pH=7.2, for 2 hours at 35° C. The full removal of the imprint molecules from the electropolymerized film was verified by monitoring the restoration of the SPR curve shift to the baseline value in 0.1 M HEPES solution.

Chemical Modification for Surface Plasmon Resonance p-Aminothiophenol-functionalized electrodes were prepared by immersing the Au slides for 24 hours into a p-aminothiophenol ethanolic solution, 50 mM. In order to prepare the bis-aniline-crosslinked AuNPs composite on the electrode, the surface-tethered p-aminothiophenol groups were electropolymerized in a 0.1 M HEPES buffer solution (pH=7.2) containing 1 mgml$^{-1}$ of p-aminothiophenol-functionalized AuNPs. The polymerization was performed by the application of 10 potential cycles between −0.35 and 0.8 V vs. Ag wire quasi-reference electrode, at a potential scan rate of 100 mVs$^{-1}$, followed by applying a fixed potential of 0.8 V for 30 minutes. The resulting films were, then, washed with the background buffer solution to exclude any residual monomer from the electrode.

Surface Plasmon Resonance Instrumentation

A surface plasmon resonance (SPR) Kretschmann type spectrometer NanoSPR 321 (NanoSPR devices, USA), with a LED light source, λ=650 nm, and with a prism refraction index of n=1.61, was used. The SPR sensograms (time-dependent reflectance changes at a constant angle) represent real-time changes and these were measured in situ using a home-built fluid cell. Au-coated semi-transparent glass slides (Mivitec GmbH, Analytical μ-Systems, Germany) were used for the SPR measurements. Prior to modification, the Au surface was cleaned in a hot ethanol, at 60° C., for 30 min. For the electrochemical polymerization and SPR measurements employing in situ constant potential application, an auxiliary Pt (0.5 mm diameter wire) and a quasi-reversible reference Ag electrode (QRE) (0.5 mm diameter wire) were installed into a Perspex cell (volume 0.5 cm$^3$, working area 0.2 cm$^2$). A PC-controlled (Autolab. GPES software) electrochemical analyzer potentiostat/galvanostat (μAutolab, type III) was employed. During the recoding of RDX in HEPES buffer, 0.1 M, pH=7.2, were injected into the SPR cell. Prior to each injection, a removal and washing of the previous sample with pure HEPES buffer was carried out, and the SPR response was re-equilibrated to the buffer baseline level).

Fitting of Experimental Results

Fresnel's equation-based SPR modeling for a five-layer system was performed using Winspall 2.0 program, generously provided by Prof. W. Knoll (Max Plank Institute for Polymer Research in Mainz, Germany). A refractive index for bulk Au, n=0.173+3.422i, was used for the modeling as the refractive index for the AuNPs. The Langmuir isotherm fittings were performed using Origin 7.5 software (Origin Lab Corporation).

Au nanoparticles (NPs), 3.5 nm, were functionalized with a capping mixed monolayer consisting of thioaniline electropolymerizable units, and with mercaptoethane sulfonic acid, to enhance the solubility of the NPs in an aqueous medium. The functionalized Au NPs were electropolymerized onto a mercaptoaniline monolayer-modified Au electrode, to yield the bis-aniline-crosslinked Au NPs matrix, FIG. 1A. Ellipsometry and coulometric analyses of the bis-aniline crosslinked Au NPs matrix, generated by the application of 10 electropolymerization cycles, indicated that the thickness of the matrix corresponded to ca. 10 nm, and that ca. $4\times10^{14}$ bis-aniline units·cm$^{-2}$ were electropolymerized on the electrode. Knowing the size of the Au NPs and the thickness of the composite, estimation was made that ca. 3 random densely packed Au NPs layers compose the matrix. Complementary Atomic Force Microscopy (AFM) measurements indicated that the height of the Au NPs composite is ca. 12±1 nm.

Figure 1B:
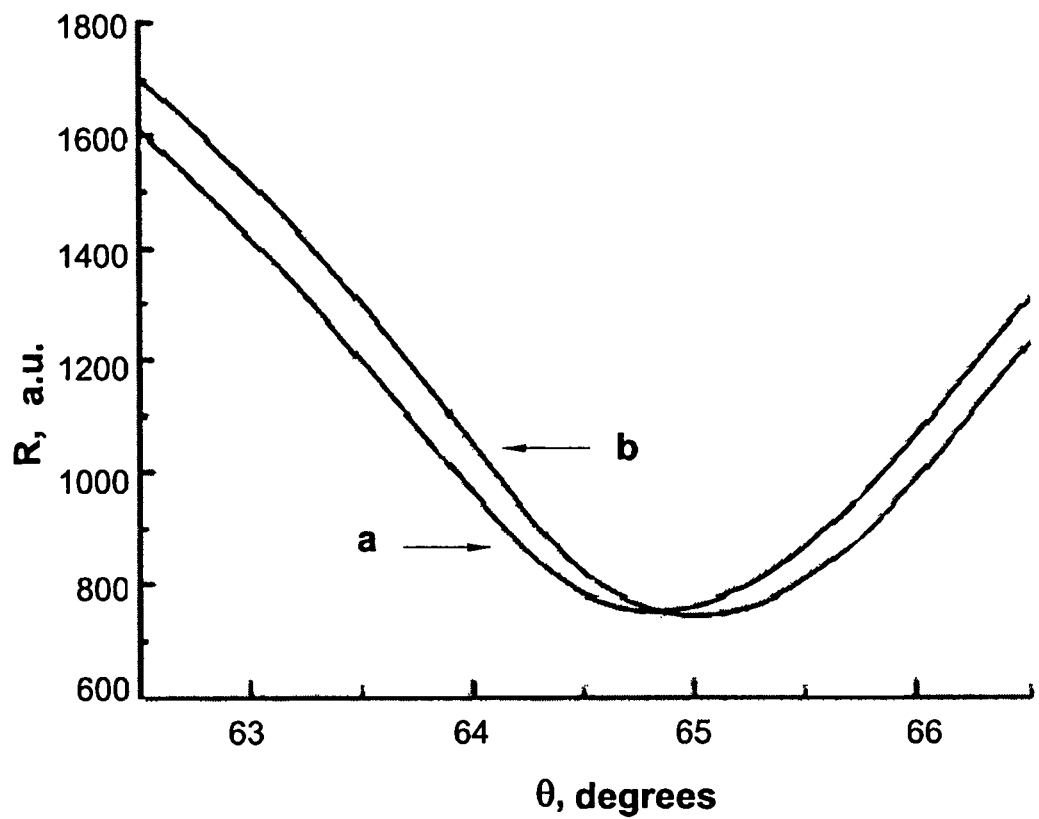
Figure 1C:
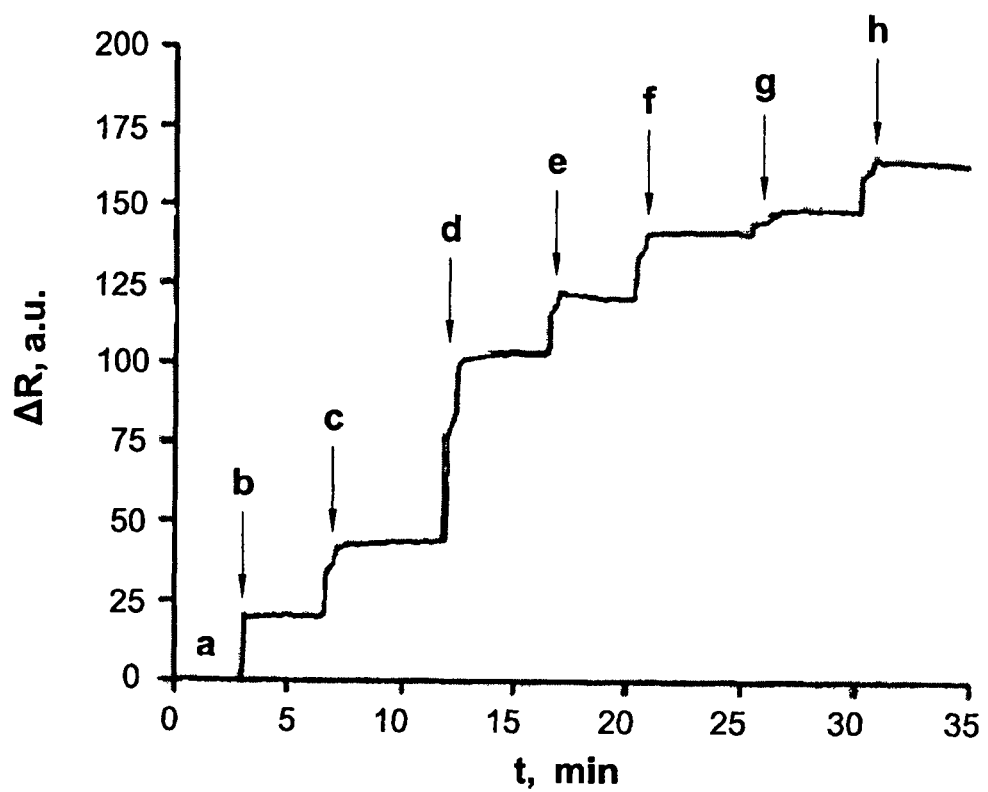
Figure 1D:
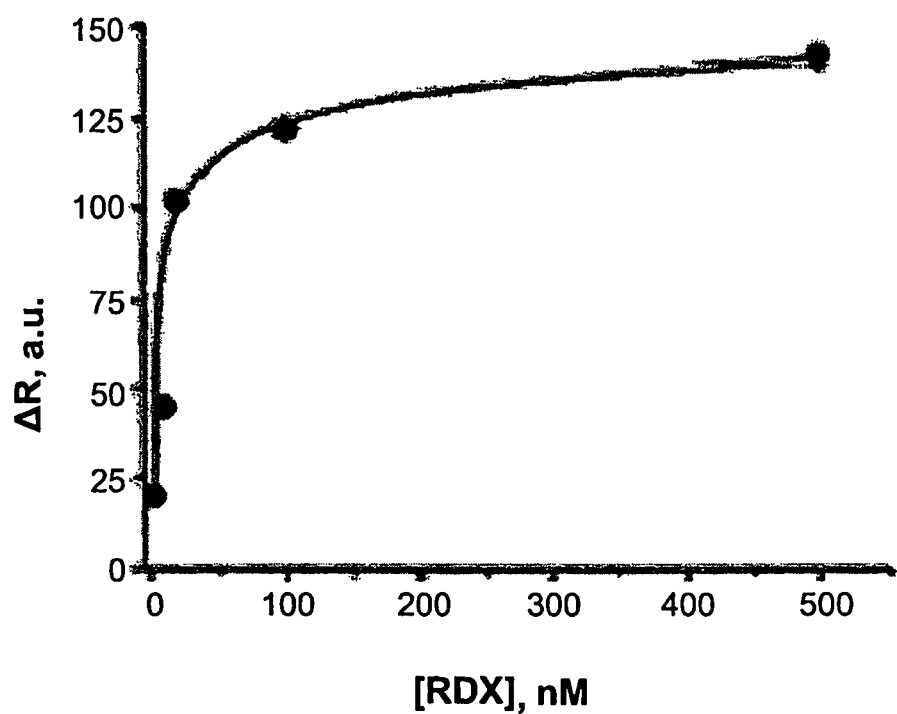
Figure 2:
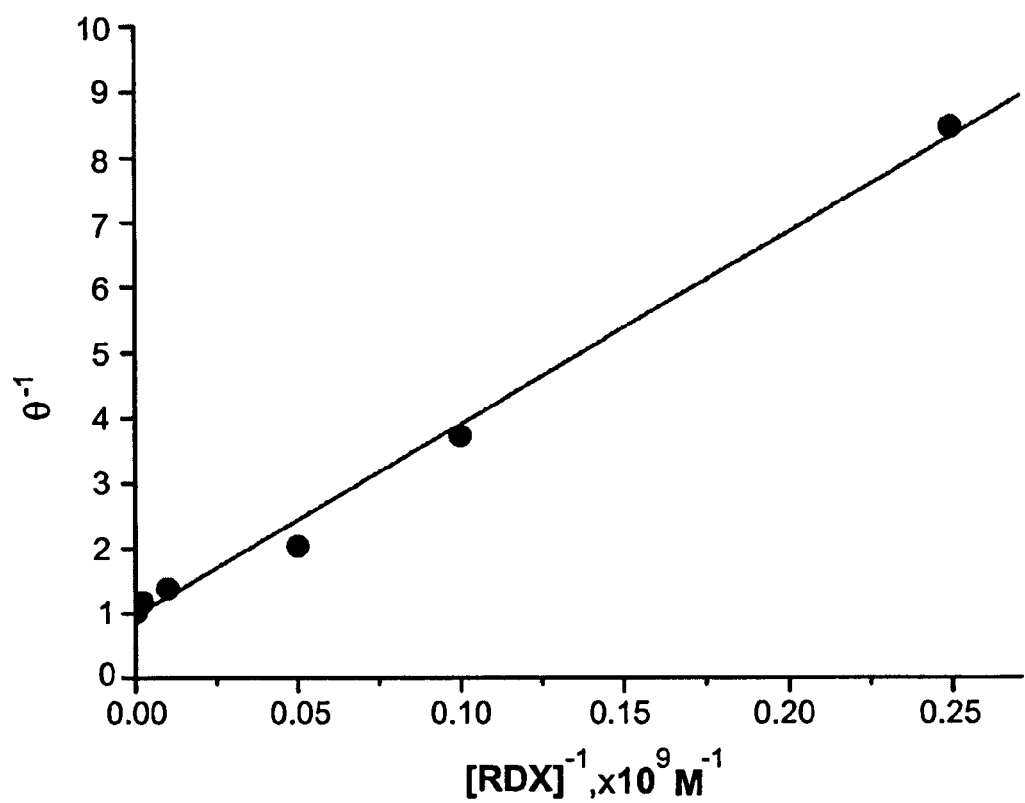
FIG. 2 is a graph showing the evaluation of the association constant between RDX and the bis-aniline-crosslinked Au NPs-functionalized electrode upon interaction of the electrode with the different bulk concentrations of RDX. The functionalized electrode was immersed in the different solutions of RDX for ca. 4 min.

The π-donor bis-aniline units bridging the Au NPs associate RDX (that includes π-acceptor nitro groups), via π-donor-acceptor interactions. The resulting charge transfer complexes alter the dielectric properties in the Au NPs matrix, resulting in an amplified shift in the surface Plasmon resonance spectrum, due to the coupling between the localized NPs plasmons and the surface plasmon wave. FIG. 1B shows the SPR curves of the Au NPs-crosslinked composite-modified surface (curve a) and after (curve b) treatment with RDX, 20 nM. The SPR curve is shifted, suggesting that the association of RDX to the matrix can be monitored by the reflectance changes of the SPR spectrum. FIG. 1C shows the sensogram corresponding to the reflectance changes of the modified surface upon treatment with variable concentrations of RDX, and the resulting calibration curve, FIG. 1D. The reflectance changes increase upon elevating the concentration of RDX and they level off to a saturation value at RDX concentration corresponding to ca. 100 nM. This result is consistent with the fact that saturation of the π-donor sites with RDX leads to a constant reflectance value. Using the Langmuir binding model, the association constant of RDX to the bis-aniline bridging units was estimated to be $K_a^{NT}=3.4\times10^7$ M$^{-1}$ (FIG. 2). The detection limit for analyzing RDX was 4 nM. In a control experiment, a two-layer structure of AuNPs was constructed, that lacked the π-donor sites on the Au surface. For this, a thiopropionic acid-capped Au NPs layer was assembled on a cystamine-modified Au surface [60]. Subsequently, a second layer of the thiopropionic acid-capped Au NPs was linked using 1,4-butane dithiol as bridging units.

The resulting two layers assembly showed a minute response only at elevated concentrations of RDX (>10 μM), implying that the π-donor-acceptor interaction between RDX and the bis-aniline units are, indeed, essential to concentrate the explosive at the surface.

The imprinting of molecular recognition sites in organic or inorganic polymer matrices is a common practice to generate selective binding sites for the imprinted substrates [61,62], and imprinted polymers for sensing were extensively used [63,64]. Thus, a possible approach to improve the sensitivity of the Au NPs composite towards the sensing of RDX involved the imprinting of specific recognition sites for this explosive in the sensing composite. The crystallographic structure of RDX reveals that this molecule adopts a chair-like configuration, with the 1,3,5-trinitro substituents in a quasi-axial position stabilized by intramolecular dipole-dipole interactions [65-67]. While it is impossible to use RDX as an imprinting molecule, due to its low solubility in the aqueous electropolymerization solution, Kemp's acid (analog 1) was selected, as an analog for RDX. The three carboxylic acid substituents in (analog 1) exhibit comparable dimensions to the nitro groups. The carboxylic acid substituents adopt axial positions due to intramolecular H-bonds, and as a result of the occupation of the equatorial positions by the bulky methyl groups. Accordingly, the electropolymerization of the Au NPs composite was conducted in the presence of a high concentration of (analog 1).

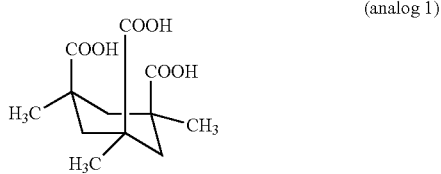
(analog 1)

Figure 3:
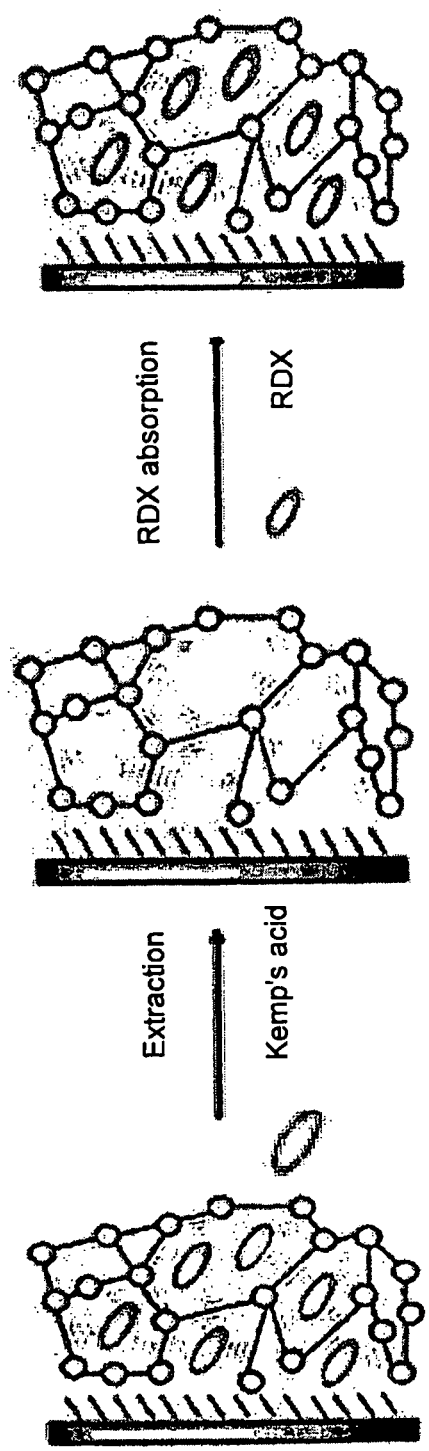
FIG. 3 is a schematic representation of the imprint of molecular recognition sites for RDX in bis-aniline-crosslinked Au NPs film polymerized at the Au electrode.
Figure 4A:
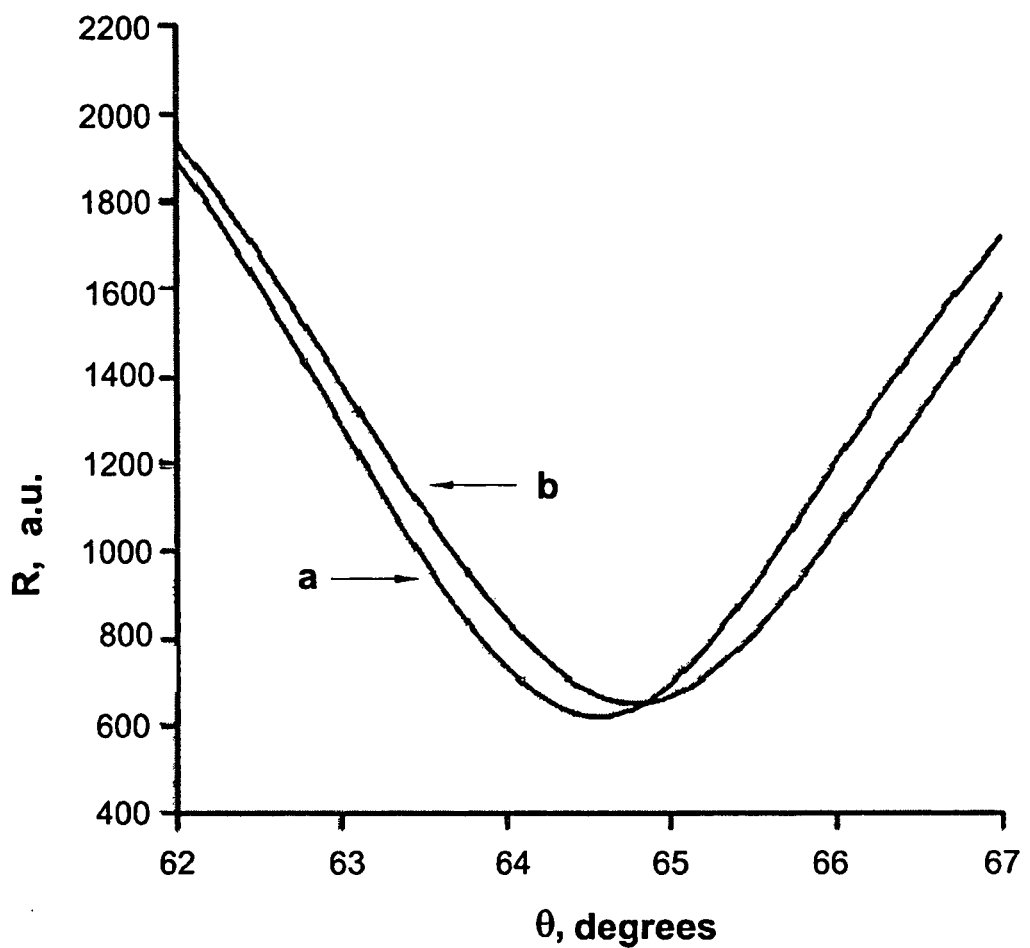
FIGS. 4A-4C are (A) SPR curves corresponding to the Kemp's acid-imprinted bis-aniline Au nanoparticles composite: (a) before the addition of RDX, and (b) after the addition of RDX, 300 fM. (B) Sensogram corresponding to changes in the reflectance intensities, at 063.3°, upon addition of variable concentrations of RDX (a) 0 fM, (b) 12 fM, (c) 50 fM, (d) 120 fM, (e) 300 fM, (f) 1 pM, (g) 2 pM. Inset: calibration curves corresponding to the analysis of RDX on (a) Kemp's acid-imprinted bis-aniline bis-aniline-crosslinked Au nanoparticles composite, and (b) cis-1,3,5-tricarboxycyclohexane-imprinted bis-aniline-crosslinked Au nanoparticles composite. The inset shows the lower concentration region of the calibration curve.
Figure 4B:
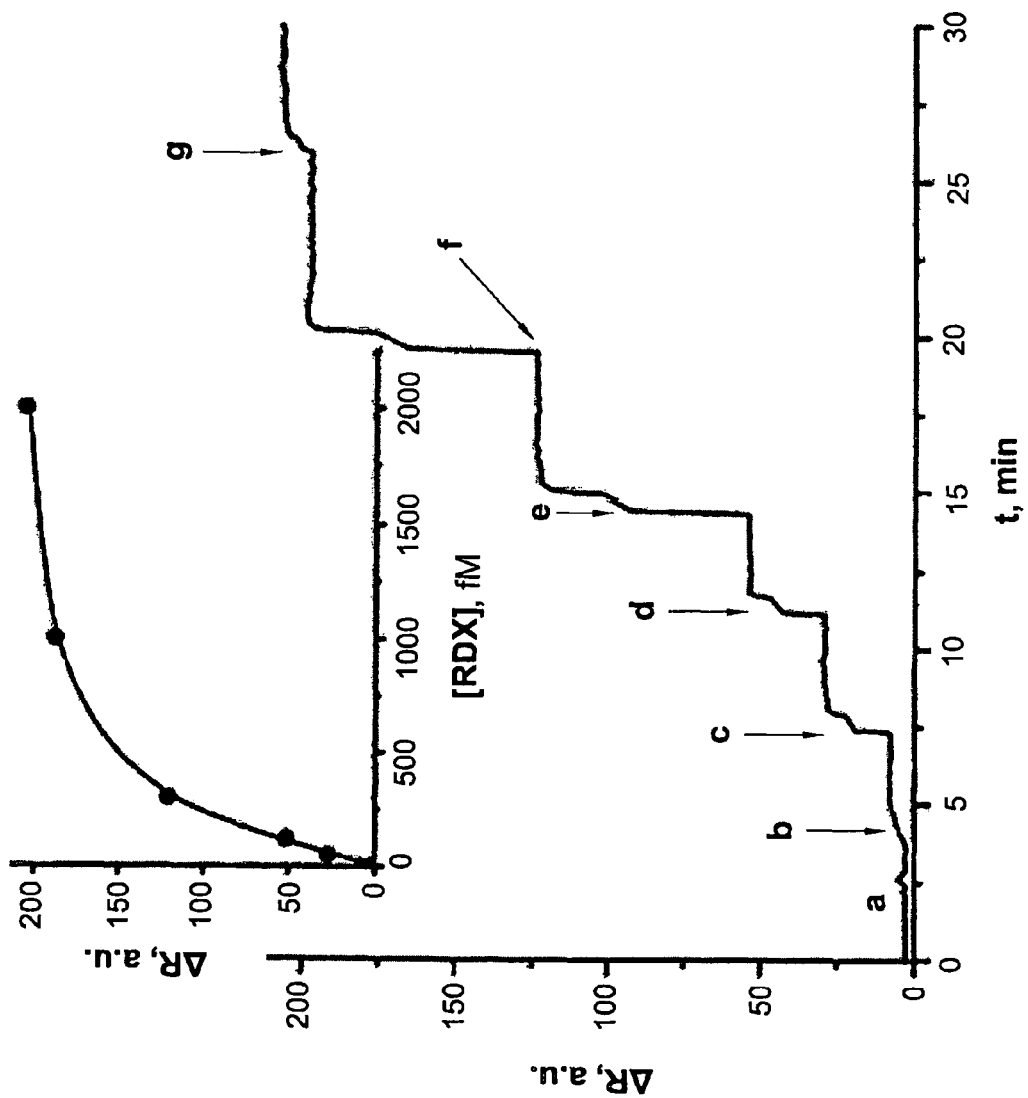

The electrostatic association of Kemp's acid to the bis-aniline bridging units suggested that eectropolymerization of the Au NPs matrix in the presence of (analog 1) yields, after the subsequent removal of the Kemp's acid, imprinted cavities of π-donor bis-aniline units with molecular contours that preferably accommodate RDX (FIG. 3). Thus, the resulting Au NPs matrix should reveal enhanced affinity for RDX due to the synergetic co-association of the explosive to the imprinted sites by π-donor-acceptor interactions, and cooperative geometrical constraints dictated by the imprinting process. FIG. 4A shows the SPR curves corresponding to the imprinted bis-aniline-crosslinked Au NPs composite before, curve (a), and after, curve (b), the addition of RDX, 300 fM. FIG. 4B depicts the sensogram corresponding to the reflectance changes of the (analog 1)-imprinted bis-aniline-crosslinked Au NPs composite upon sensing variable concentrations of RDX, and the resulting calibration curve. As the concentration of RDX increases, the reflectance changes become higher, and they level-off at a concentration corresponding to ca. 1 pM. The detection limit for analyzing the (analog 1)-imprinted Au NPs matrix is 12 fM. It should be noted, that the imprinted composite reveals a 4×10^5-fold lower detection limit for RDX, as compared to the non-imprinted sensing matrix. The association constant for RDX to the imprinted sites is extracted from the calibration curve—$K_a^I=1.9\times10^{12}$ M$^{-1}$. Thus, the enhanced sensitivity of the imprinted composite is attributed to the improved association of RDX to the imprinted sites, resulting from the steric confinement of the explosive molecules to the imprinted molecular contours consisting of the π-donor bridging units.

The (analog 1)-imprinted Au NPs composite demonstrates, also, selectivity towards the analysis of RDX. It was found that the non-imprinted Au NPs array reveals a low detection limit for sensing TNT as compared to RDX (10 pM vs. 4 nM, respectively). This is attributed to the fact that TNT is substantially better electron acceptor as compared to RDX ($K_a^{NI}$(TNT)=3.9×10$^9$ M$^{-1}$ vs. $K_a^{NI}$(RDX)=3.4×10$^7$ M$^{-1}$). The (analog 1)-imprinted matrix, however, demonstrates impressive selectivity for detecting RDX, and provides quantitative SPR response for analyzing RDX up to a concentration of 1 pM, with a detection limit of 12 fM. Furthermore, the (analog 1)-imprinted composite response to TNT concentrations which are only higher than 30 pM. It was also found that the Kemp's acid-imprinted Au NPs matrix is highly selective. Nitroaromatic substrates of weaker acceptor properties such as 2,4-dinitrotoluene or 4-nitrotoluene exhibit small reflectance changes at concentrations higher than 10 μM. Other aromatic substances that lack n-acceptor features such as 4-hydroxy toluene, aniline or salicylic acid did not affect the SPR response for the composite even at high concentrations, 1×10$^{-4}$ M. Also, different anions such as $PO_4^{2-}$, $NO_3^-$ or $SO_4^{2-}$ did not affect the SPR response upon analyzing RDX.

The successful selection of Kemp's acid as a molecular imprint analog for RDX was highlighted by an additional experiment, where cis-1,3,5-hexane tri-carboxylic acid, (analog 2), was used as the imprint molecule.

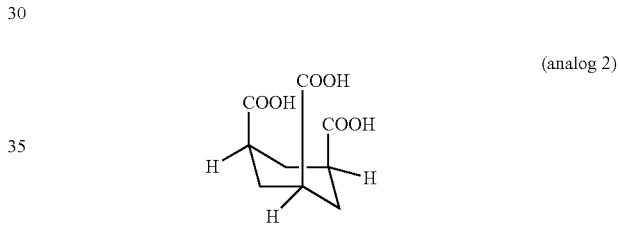
(analog 2)

Figure 4C:
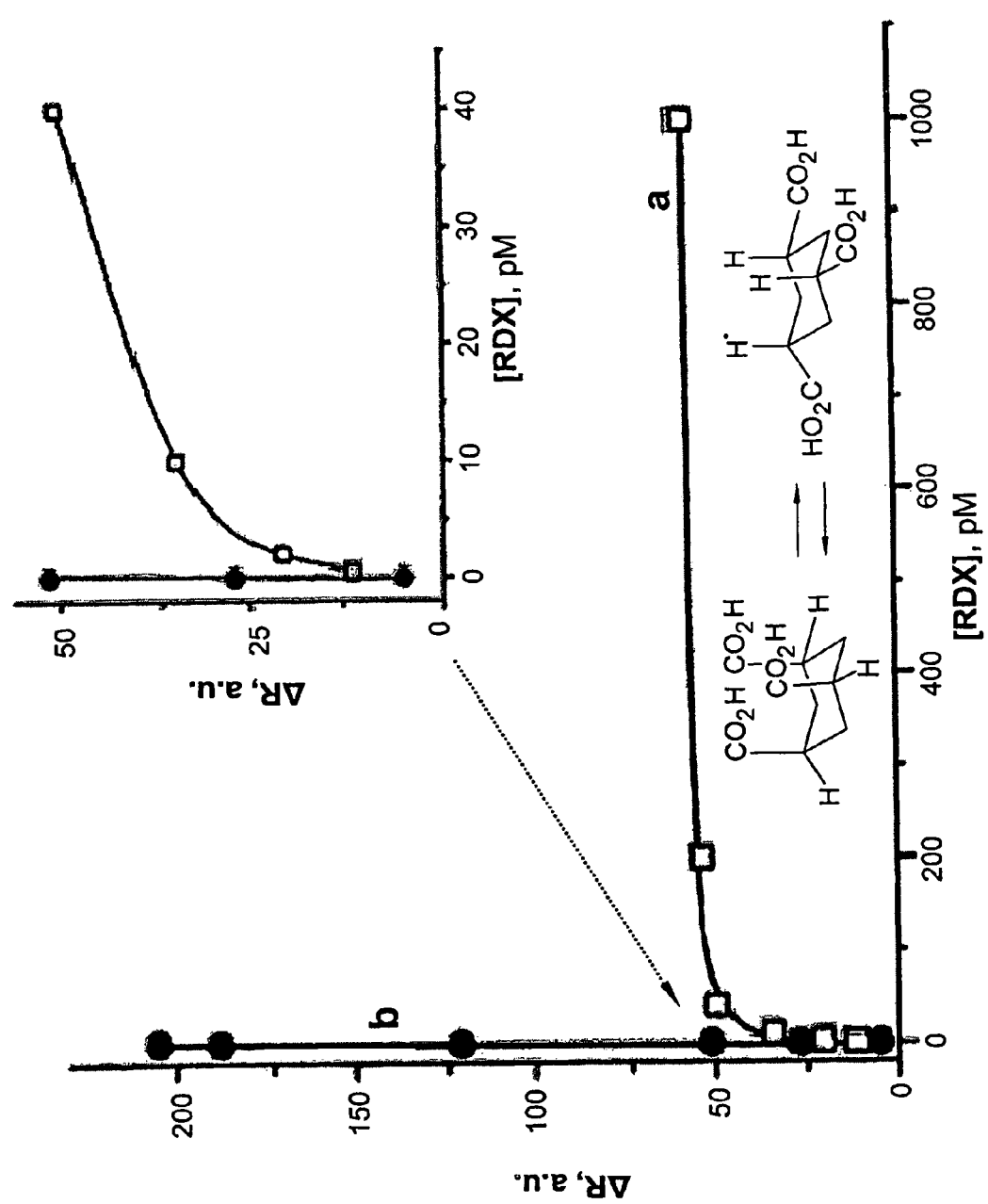
Figure 5:
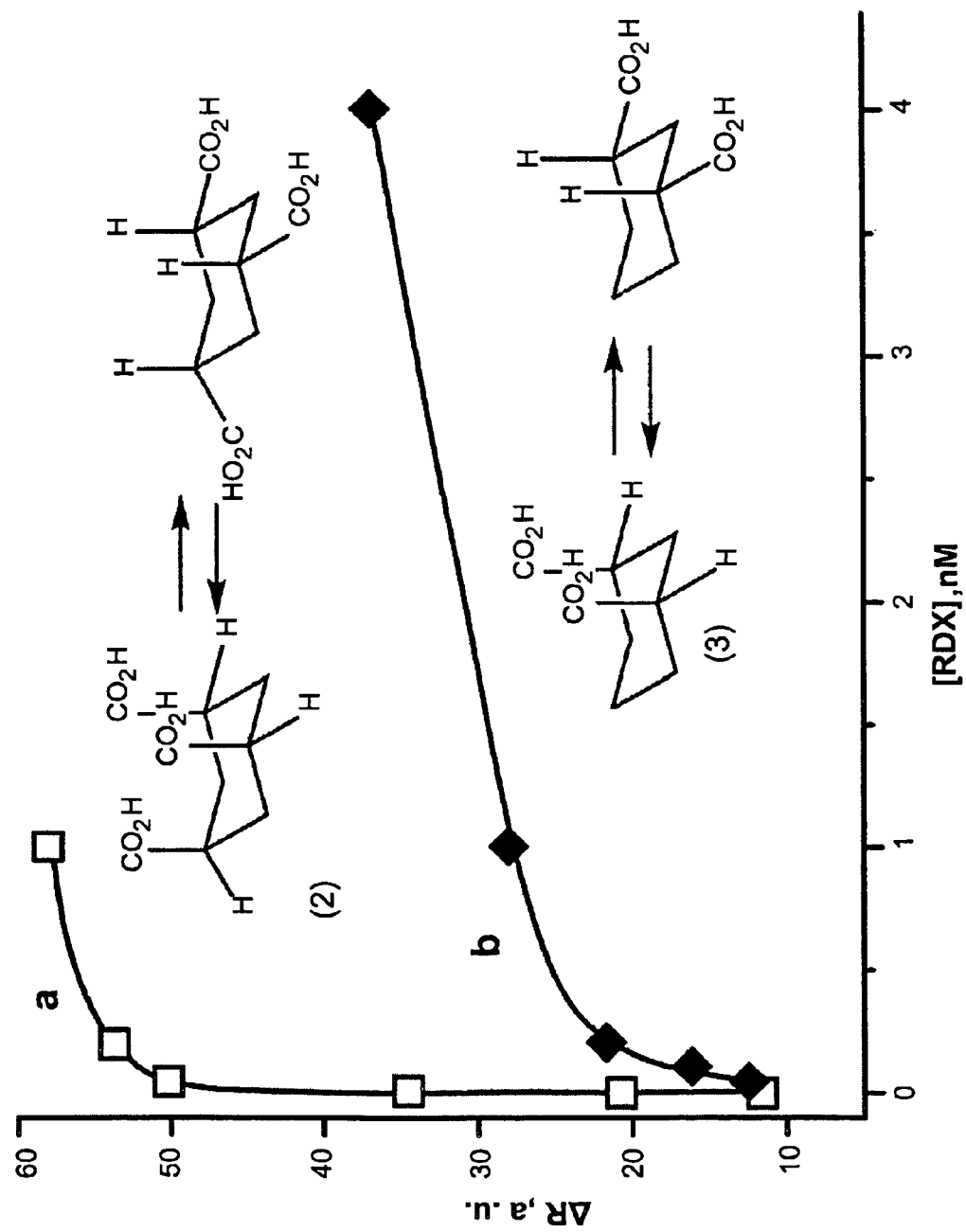
FIG. 5 is presents calibrations curves corresponding to the analysis of RDX on (a) cis-1,3,5-tricarboxycyclohexane-imprinted composite, and (b) cis-1,3-dicarboxy cyclohexane-imprinted composite. Measurements were performed in a 0.1 M HEPES buffer, pH=7.2.

This latter compound lacks the three equatorial methyl groups, and exhibits conformational flexibility. As a result, the population of the imprinted sites is lower, and the structural fits of the sites (the molecular contour) towards RDX are expected to be less effective. FIG. 4C depicts the calibration curves corresponding to the analysis of RDX by the (1)-imprinted and the (2)-imprinted Au NPs composites. Evidently, the analysis of RDX by the (2)-imprinted composite reveals a less effective detection limit, 500 fM, and a substantially lower saturation value of the reflectance changes. These results are consistent with the fact that (2) exhibits conformational flexibility, and thus, the imprinting procedure yields imprinted sites of lower quality molecular contours (higher detection limit), and lower saturation reflectance values (FIG. 5).

Figure 6:
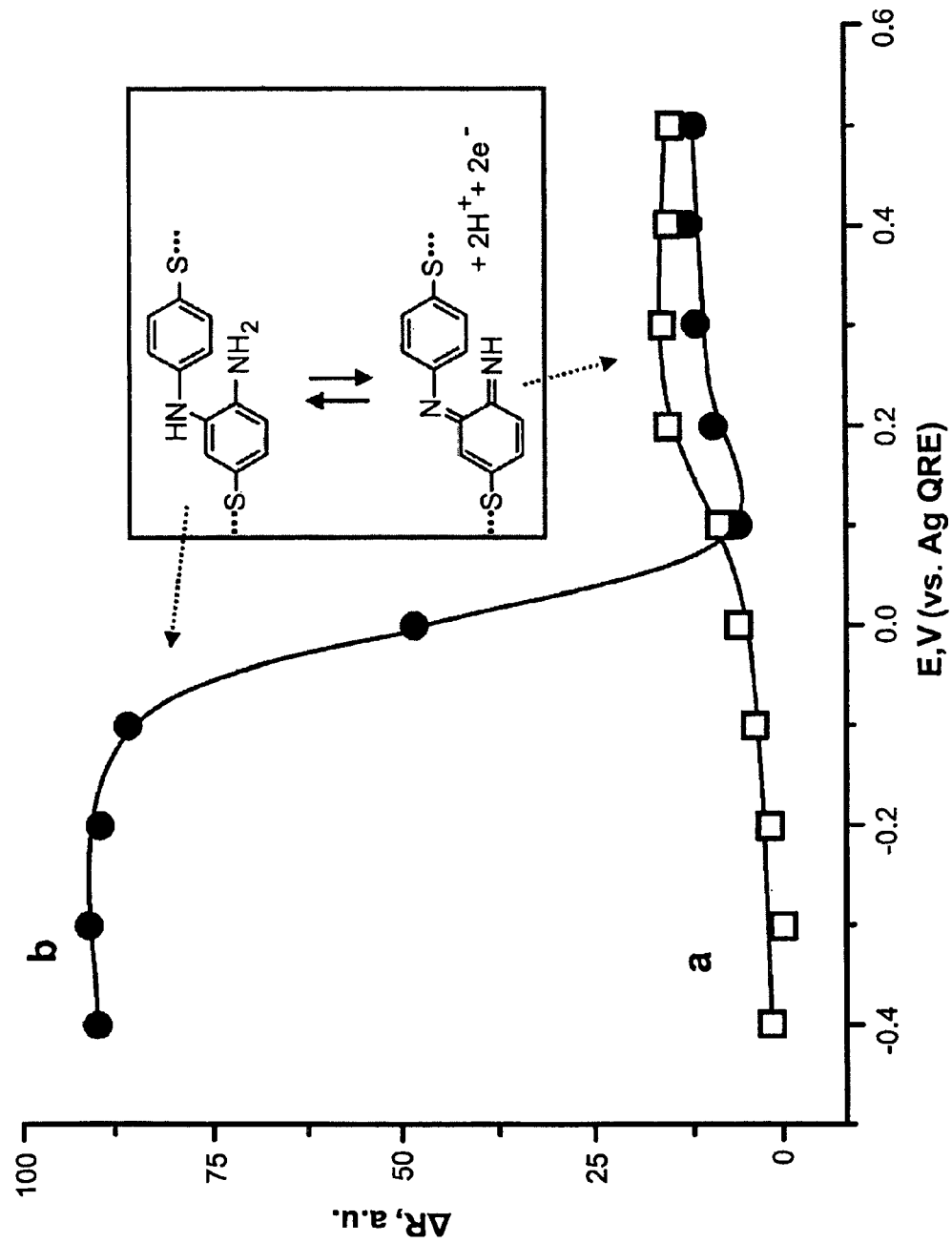
FIG. 6 is a diagram of the effect of applied potential on the reflectance changes, at θ=63.3°, of the Kemp's acid-imprinted bis-aniline-crosslinked Au nanoparticles composite: (a) The imprinted composite in a pure 0.1M HEPES buffer solution, pH=7.2, and (b) The imprinted composition in a 0.1 M HEPES buffer solution, pH=7.2, that includes RDX, 300 fM. Inset: the redox states of the bis-aniline bridges.

A further support that the concentration of RDX at the Au surface originated from π-donor-acceptor interactions of the explosive with the bis-aniline bridging units was obtained by probing the effect of the applied potential on the SPR response of the modified surface in the absence and presence of RDX. The bis-aniline units crosslinked the Au NPs exhibit a quasi-reversible redox wave at E~0.1 V vs. Ag quasi reference electrode (QRE), pH=7.2, in accord with the redox process depicted in FIG. 6. Thus, at E<0.1 V the bis-aniline bridges exist in their reduced π-donor state, whereas at E>0.1 V, the bridges are present in a quinoid-type π-acceptor configuration. Accordingly, the analysis of RDX is controlled by the applied potential, provided that π-donor-acceptor interactions play a role in the concentration of the explosive at the surface. FIG. 6, curve (a), depicts the reflectance changes observed for the (1)-imprinted matrix under different bias potentials. Only minute reflectance changes are observed upon transferring the oxidized quinoid-bridged state (at $E>0.1$ V) to the reduced bis-aniline state ($E<0.1$ V). FIG. 6, curve (b), shows the effect of the applied potential on the reflectance values of the modified surface in the presence of RDX, 120 fM. At potentials negative to $E=0.1$ V, the reflectance changes exhibit high values, while low values are obtained as the applied potential is shifted more positively these results are consistent with the fact that at $E<0.1$ V, the bis-aniline units bind the RDX to the matrix, whereas at $E>0.1$ V, the affinity interactions of RDX with the composite are depleted, eliminating the ability to sense the explosive.

The invention claimed is:

1. A method for determining the presence and/or concentration of non-aromatic non-planar nitroamine analyte molecules in a sample, said method comprising:
    providing a matrix of a plurality of transition metal nanoparticles (TMNPs), each carrying a plurality of electropolymerizable recognition groups composed of electropolymerizable thioaniline dimer, 4-amino-3-(4-mercaptophenylamino)benzenthiol,
    said matrix comprising analyte-recognition fields complementary to said non-aromatic non-planar nitroamine analyte molecules;
    contacting said matrix with a sample suspected of containing said non-aromatic non-planar analyte molecules; said recognition groups being capable of undergoing a physical and/or chemical interaction with said analyte molecules; and
    monitoring at least one of a measurable chemical or a physical change in said matrix resulting from an interaction between said analyte molecules and said recognition groups;
    wherein said at least one of a chemical and a physical change is indicative of at least one of presence and quantity of said analyte in the sample.

2. The method according to claim 1, wherein the TMNPs in said plurality of TMNPs are associated with one another through said recognition groups.

3. The method according to claim 1, wherein said nanoparticles are metal selected from the group consisting of platinum (Pt), palladium (Pd), iridium (Ir), gold (Au), silver (Ag), nickel (Ni), titanium (Ti), and alloys thereof.

4. The method according to claim 3, wherein said TMNPs are one of gold nanoparticles and nanoparticles containing gold metal.

5. The method according to claim 2, wherein said TMNPs are associated with the recognition groups via at least one reactive group selected from the group consisting of —S, —$NH_2$ and —$CO_2^-$.

6. The method according to claim 5, wherein the reactive group —S is a sulfur containing group.

7. The method according to claim 6, wherein said sulfur containing group is selected from the group consisting of thioaniline, thioaniline dimer and oligomers thereof.

8. The method according to claim 1, wherein the nitroamine compound analyte is selected from the group consisting of hexahydro-1,3,5-trinitro-1,3,5-triazine (RDX), octahydro-1,3,5,7-tetranitro-1,3,5,7-triazocine (HMX), 2,4,6,8,10,12-hexanitro-2,4,6,8,10,12-hexaazaisowurtzitan (CL-20), and combinations thereof.

9. The method according to claim 8, wherein the nitroamine analyte is hexahydro-1,3,5-trinitro-1,3,5-triazine (RDX).

10. The method according to claim 1, wherein said matrix is associated with an active surface.

11. The method according to claim 10, wherein said active surface is conductive.

12. The method according to claim 11, wherein said active surface is composed of a metal selected from the group consisting of gold, platinum, silver, and alloys thereof.

13. The method according to claim 11, wherein said active surface is selected from the group consisting of graphite, Indium-Tin-Oxide (ITO), conductive glass, glass coated with a metal, glass coated with a metal alloy, and an electrode.

14. A method for determining the presence and/or concentration of non-aromatic non-planar analyte molecules in a sample, comprising:
    (a) providing nanoparticles of a transition metal, said nanoparticles carrying a plurality of recognition groups composed of electropolymerizable thioaniline dimer, 4-amino-3-(4-mercaptophenylamino)benzenthiol capable of undergoing interaction with non-aromatic non-planar analyte molecules;
    (b) contacting said nanoparticles with a sample suspected of containing said analyte molecules;
    (c) establishing assay conditions to enable interaction between said recognition groups and the analyte molecule(s);
    (d) probing the interaction to detect at least one change in at least one dielectric property in the vicinity of the nanoparticles;
    (e) sensing any detected change; and
    (f) providing an indication of a detected change;
    whereby said change is indicative of at least one of the presence and quantity of said non-aromatic non-planar analyte molecule(s) in the sample.

15. An electrode for carrying out detection of a non-aromatic non-planar nitroamine analyte in a sample comprising a matrix of a plurality of transition metal nanoparticles (TMNPs), each carrying a plurality of electropolymerizable recognition groups composed of electropolymerizable thioaniline dimer, 4-amino-3-(4-mercaptophenylamino)benzenthiol; said matrix including analyte-recognition fields complementary to the non-aromatic non-planar nitroamine analyte molecules;
    whereby when a sample suspected of containing the non-aromatic non-planar analyte molecules is contacted with said matrix, said recognition groups undergo a physical and/or chemical interaction with the non-aromatic non-planar analyte molecules that can be monitored to detect a measurable chemical or a physical change in said matrix indicative of presence or quantity of the non-aromatic non-planar analyte molecules in the sample.

16. A device for carrying out detection of a non-aromatic non-planar nitroamine analyte in a sample, said device comprising at least one assay unit having a plurality of nanoparticles of a transition metal, said nanoparticles carrying recognition groups composed of electropolymerizable thioaniline dimer 4-amino-3-(4-mercaptophenylamino)benzenthiol capable of undergoing interaction with the analyte molecule(s), under predetermined assay conditions;
    whereby to detect and indicate the presence of non-aromatic non-planar nitroamine analyte in said sample.

* * * * *